US010189811B2

(12) United States Patent
Rey et al.

(10) Patent No.: US 10,189,811 B2
(45) Date of Patent: Jan. 29, 2019

(54) METHOD FOR PREPARING THE ANHYDROUS CRYSTALLINE FORM OF ISONIAZID-DERIVED HYDRAZONE, THUS PRODUCED CRISTALLINE POLYMORPH OF THE ANHYDROUS FORM, USE THEREOF FOR THE TREATMENT OF ALZHEIMER'S DISEASE, PARKINSONISM AND OTHER NEURODEGENERATIVE DISORDERS, AND PHARMACEUTICAL COMPOSITION

(71) Applicant: FACULDADES CATÓLICAS, Associação sem fins Lucrativos, Mantenedora da Pontifícia Universidade, Rio de Janeiro (BR)

(72) Inventors: Nicolás Adrián Rey, Rio de Janeiro (BR); Leonardo Viana de Freitas, Rio de Janeiro (BR)

(73) Assignee: FACULDADES CATÓLICAS, Associação sem fins Lucrativos, Rio de Janeiro (BR)

( * ) Notice: Subject to any disclaimer, the term of this patent is extended or adjusted under 35 U.S.C. 154(b) by 0 days.

(21) Appl. No.: 15/106,181

(22) PCT Filed: Jun. 6, 2014

(86) PCT No.: PCT/BR2014/000186
§ 371 (c)(1),
(2) Date: Jun. 17, 2016

(87) PCT Pub. No.: WO2015/089599
PCT Pub. Date: Jun. 25, 2015

(65) Prior Publication Data
US 2017/0158665 A1 Jun. 8, 2017

(30) Foreign Application Priority Data
Dec. 20, 2013 (BR) .............. 102013033006

(51) Int. Cl.
*C07D 401/12* (2006.01)
*C07D 215/24* (2006.01)

(52) U.S. Cl.
CPC ........ *C07D 401/12* (2013.01); *C07D 215/24* (2013.01); *C07B 2200/13* (2013.01)

(58) Field of Classification Search
CPC .................................................. C07D 401/12
See application file for complete search history.

(56) References Cited

FOREIGN PATENT DOCUMENTS

CH          349599        * 12/1960

OTHER PUBLICATIONS

Y-C Liu et al., Journal of Inorganic Biochemistry (Jul. 9, 2009).*
Y-C Liu et al., 103 Journal of Inorganic Biochemistry, 1014-1022 (2009).*
Y-C Liu et al., 12 Inorganic Chemistry Communications, 704-706 (2009).*
Y-C-Liu et al., 694 Journal of Organometallic Chemistry, 3091-3101 (2009).*
Y-C Liu et al., 22 BioMetals, 733-751 (2009).*
Y.C. Liu et al., 44 European Journal of Medicinal Chemistry, 5080-5089 (2009).*
Y-C Liu et al., 147 Journal of Biochemistry, 381-391 (2010).*
Y-C Liu et al., 64 Applied Spectroscopy, 980-985 (2010).*
Y-C Liu et al., 64 Australian Journal of Chemistry, 345-354 (2011).*
L. Viana de Freitas et al., 116 Spectrochimica Acta Part A: Molecular and Biomolecular Spectroscopy, 41-48 (2013).*
Machine Translation of CH 349,599 (1960).*
Solid State Characterization of Pharmaceuticals 427-450 (R.A. Storey et al., eds., 2011).*

* cited by examiner

*Primary Examiner* — Alexander R Pagano
(74) *Attorney, Agent, or Firm* — Laurence P. Colton; Smith Tempel Blaha LLC

(57) ABSTRACT

The present invention relates to the method for preparing the anhydrous crystalline form of isoniazid-derived hydrazone (8-hydroxyquinoline-2-carboxaldehyde isonicotinoyl hydrazone), to the thus produced polymorph and to the use thereof for the treatment of Alzheimer's disease and parkinsonism, inter alia, and to a pharmaceutical composition.

6 Claims, 7 Drawing Sheets

METHOD FOR PREPARING THE ANHYDROUS CRYSTALLINE FORM OF ISONIAZID-DERIVED HYDRAZONE, THUS PRODUCED CRISTALLINE POLYMORPH OF THE ANHYDROUS FORM, USE THEREOF FOR THE TREATMENT OF ALZHEIMER'S DISEASE, PARKINSONISM AND OTHER NEURODEGENERATIVE DISORDERS, AND PHARMACEUTICAL COMPOSITION

FIELD OF THE INVENTION

The present invention regards the preparation method of the anhydrous crystalline form of an isoniazid-derived hydrazone (namely, 8-hydroxyquinoline-2-carboxaldehyde isonicotinoyl hydrazone, or INHHQ), the polymorph produced and its use, in any pharmaceutical composition, for the treatment of Alzheimer's and Parkinson's diseases, as well as other neurodegenerative disorders.

BACKGROUND OF THE INVENTION

With the general increase in life expectancy recorded in recent times, especially in developed countries, the prevalence of certain neurodegenerative diseases has been observed. Alzheimer's disease (AD), first characterized in 1906 by the german neuropathologist Alois Alzheimer, is currently the most common one. It is a primarily age-related disease and the most common cause of dementia in older people. Dementia is characterized by progressive loss of memory and cognitive functions, among other diagnostic criteria, being most of them present in the Diagnostic and Statistical Manual of Mental Disorders and described on the National Institute of Neurological and Communicative Disorders Association.

The disease has two general classifications: 1) late onset, which occurs with the highest incidence at about 60 years of age, and 2) early onset, occurring around 40 years. In the US and Great Britain, it represents about 50% of cases of dementia, being estimated that it is the fourth leading cause of deaths of elderly in these countries. Regarding the neuropathological aspect, patients show diffuse cortical atrophy, presence of senile plaques and neurofibrillary tangles, neurovascular degeneration and neuronal loss.

These senile plaques are characterized mainly by the presence of fibrillar deposits of β-amyloid peptide (Aβ), consisting of approx. 40 amino-acid residues. It has been observed high concentration of physiological metal ions such as $Zn^{2+}$ and $Cu^{2+}$, in these plaques, which is considered indicative that the interaction of Aβ with these biometais is at the heart of events that lead to aggregation and toxicity of this peptide. The ferric ions, in turn, have also been related to the aggregation of neurofibrillary tangles, in addition to contributing to the oxidative processes that occur in the nerve cells of the body. Something similar occurs in Parkinson's disease with the protein α-synuclein.

The already approved drugs for the treatment of AD are intended to combat deficits associated with reduced cerebral function and fall into two classes: acetylcholinesterase inhibitors and inhibitors of NMDA (N-Methyl-D-Aspartate) receptors. Such drugs seem to act in enhancing the remain of the cognitive function, however, are not able to prevent the progression of the disease, being, therefore, important the development of new therapeutic agents that hold the advance of neurodegeneration as well as, as far as possible, promote their regression. In this sense, an interesting approach is to obtain compounds that inhibit, specifically, abnormal metal-protein interactions. This class of drugs is known as MPACs (metal-protein attenuating compounds) and relate to the allocation and distribution normalization of physiological metal ions.

A classic example is the clioquinol (CQ or PBT1), a substance belonging to the group of 8-hydroxyquinolines, which, however, was abandoned due to certain unwanted side effects, such as subacute myelo-optic neuropathy.

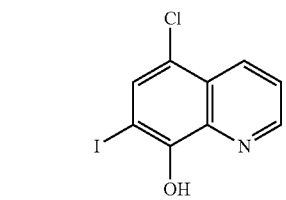 [SMILES: Oc1c(I)cc(Cl)c2cccnc12]

Structure of clioquinol
(5-chloro-7-iodo-8-hydroxyquinoline)

8-hydroxyquinoline-2-carboxaldehyde isonicotinoyl hydrazone (or INHHQ) was first described in a series of publications from the year 2009, in which its interactions with some rare earths ions, namely, dysprosium(III), europium(III), holmium(III), neodymium(III), and ytterbium(III) were examined. Erbium(III) and terbium(III) complexes were reported in 2010, while the samarium(III) compound was described in 2011. In those works, its rare earths complexes, and not INHHQ itself, were proposed as potential anticancer drugs, since they bind to DNA through an intercalation mechanism, besides they possess antioxidant properties, scavenging hydroxyl and superoxide radicals. Although the method of preparation described by the authors of those papers, Liu & Yang, is similar to the one employed by us, some experimental details are different. Mainly, the use of acid catalysis (drops of concentrated hydrochloric acid) allow us to reduce the reflux period to just an hour. On the other hand, and more important yet, the use of methanol PA ACS (99.8%) in the recrystallization step, instead of the methanol:water 80:20 used by the Chinese authors, lead to the preparation of the anhydrous crystalline form of the compound, which is completely original. Although this is not commented in the original articles, data suggest that the Chinese authors worked with an hydrated form of INHHQ, different from the one obtained by us, which can be clearly seen in the major differences between the melting points of the compounds, as well as between the vibrational (FTIR and Raman) spectra of both samples. Besides, application of INHHQ in the treatment of neurodegenerative diseases is completely new.

The anhydrous crystalline form described herein is characterized by its melting point, elemental analysis, crystal structure (single-crystal diffraction), powder diffraction pattern, and vibrational spectra.

BRIEF DESCRIPTION OF THE DRAWINGS

The present invention will hereinafter be illustrated with reference to the attached figures, which represent:

FIG. 2: Perspective views of INHHQ showing: (a) the hydrogen-bonding network, (b) the π-π and the O1-H12 ... π stacking interactions and (c) the 3D crystalline packing along the crystallographic axis a;

BRIEF DESCRIPTION OF THE INVENTION

Figure 1:
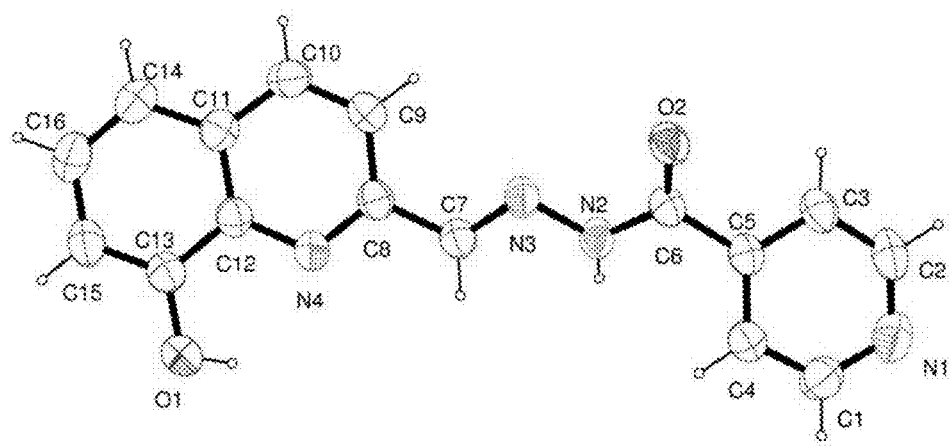
FIG. 1: ORTEP representation of the compound INHHQ, showing the identification scheme of the constituent atoms.

In the search for new MPACs, more effective and safer for patients, a hydrazone derived from the mycobactericidal agent isoniazid was produced, characterized in its crystalline form and successfully tested in modulating in vitro the interaction between β-amyloid peptide (or α-synuclein) and the physiological metals copper and zinc, which can have great impact on the treatment of Alzheimer's and Parkinson's diseases, as well as in other related diseases.

DETAILED DESCRIPTION OF THE INVENTION

The isonicotinoyl hydrazone of 8-hydroxyquinoline-2-carboxaldehyde (or INHHQ) was synthesized, completely characterized in its anhydrous crystalline form and successfully tested in modulating the in vitro interaction between β-amyloid peptide (or α-synuclein) and the physiological metals copper and zinc, which can have applications in the treatment of Alzheimer's and Parkinson's diseases, amongst other neurodegenerative diseases (such as Huntington's).

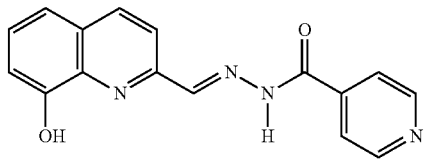 [SMILES: O=C(N/N=C/c1ccc2cccc(O)c2n1)c1ccncc1]

Structure of INHHQ
(8-hydroxyquinoline-2-carboxaldehyde isonicotionoyl hydrazone)

Connected to the 8-hydroxyquinoline portion, characteristic of CQ, INHHQ also contains the mycobactericidal drug isoniazid (INH), resulting in a potentially interesting hydrazone capable of coordinating metal ions of biological importance through its various N/O-donor sites. Furthermore, linking two molecules that have, individually, specific activity, creating a single species, has been an attractive approach to rational drug development, since a combination of the two original activities can be expected of the hybrid molecule. Besides, isoniazid-derived hydrazones are well known as iron chelating agents. However, to the best of our knowledge, there are no studies in the literature involving the coordination of INHHQ to any transition metal.

In the context of the treatment of AD and Parkinson's disease, the coordination capacity of the ligand to essential transition metals (such as copper, zinc and iron) must be better understood. As a first approach to this problem, we present the results of a spectroscopic vibrational (FTIR/Raman) and a single-crystal X-ray diffraction structural study on the 8-hydroxyquinoline-2-carboxaldehyde isonicotinoyl hydrazone, obtained through the process herein described and claimed, including its crystal structure, vibrational spectra and their full assignment by computational methods based on the Density Functional Theory (DFT).

Preparation Methodology of the Anhydrous Crystalline Form of 8-hydroxyquinoline-2-carboxaldehyde isonicotinoyl hydrazone To 25 mL of a 8-hydroxyquinoline-2-carboxaldehyde (1.04 g, 6.0 mmol) solution in ethanol, 25 mL of ethanolic solution of isoniazid (0.82 g, 6.0 mmol) were dropwise added. Two drops of concentrated hydrochloric acid were added as a catalyst for the reaction. After refluxing for 1 h, the mixture was cooled to room temperature and the yellow precipitate obtained was filtered and vacuum dried. Next, the product was recrystallized in hot methanol methanol PA ACS (99.8%). A pale yellow crystalline solid was obtained after cooling and dried at room temperature. After few days, single-crystals of INHHQ were isolated from the mother liquor. Total yield of the process: 0.98 g (56%).

Characterization:
m.p.: 246-249° C.

Elemental analysis: calculated for $C_{16}H_{12}O_2N_4$: C, 65.7%; H, 4.1%; N, 19.2%—found: C, 66.3%; H, 4.1%; N, 19.4%.

Main IR bands (KBr, cm$^{-1}$): 3396 (ν OH); 3183 (ν NH); 1656 (ν C=O+β NH); 1647 (ν C=N azomethine group); 1556 (ν C=N e ν C=C from the quinolinic ring) and 1545 (ν C=C e ν C=N from the pyridinic ring).

X-Ray Diffraction Analysis

The X-ray diffraction (XRD) was performed using an appropriate single-crystal of INHHQ. The sample was measured on a diffractometer Enraf-Nonius Kappa-CCD with Mo K$_\alpha$ (λ=0.71073 Å) radiation. The unit cell parameters were based on all reflections. Data were collected at room temperature (293 K) using the computer program Collect being the integration and scaling of reflections made with Denzo-Scalepach system of HKL programs. The crystal structure was solved by direct method with SHELXS-97 and the atoms, except hydrogens, were anisotropically refined by the least squares method on F2 using the SHELXL-97 program. All aromatic and hydroxyl group's hydrogen atoms were placed in the calculated positions (C—H: 0.98 Å, O—H: 0.82 Å). Shift factors were taken as $U(H)_{isot}$=1.2/1.5 Uhost. The H atoms attached to the C7 carbon and N2 nitrogen were located in the Fourier difference map and refined freely. The computer programs ORTEP-3 and Mercury (version 2.3) were used to draw the structures. On the other hand, powder X-ray diffraction experiments were performed in a Bruker D8 Discover XRD equipment using copper radiation. Experimental conditions: tension of 40 kV and current of 40 mA. The Bragg-Brentano geometry was used.

Spectroscopic Analyses

IR spectra were obtained on a Perkin-Elmer 2000 FT-IR spectrometer, using KBr sampling. On the other hand, the Raman spectra of the solid sample were measured on a Perkin-Elmer 400 Station equipment, using the 785 nm line for excitation.

DFT Calculations

The first step was to conduct a search of the conformational space of 8-hydroxyquinoline-2-carboxaldehyde isonicotinoyl hydrazone using the semi-empirical PM3 method, as implemented in the SPARTAN'02 software, with the following set of parameters: Max-Confs=100; window=10 kcal mol$^{-1}$; model=PM3. A total of 12 different conformations were found. The lowest energy conformation was of 41.387 kcal mol$^{-1}$. From this distribution, 5 conformations were selected for analysis by DFT. These conformations will be called, from now on, from Conf. 1 to Conf. 5.

After the selection of these five conformations, a complete geometry optimization, without limitation, using the default convergence criteria and calculation of harmonic vibrational frequencies, was performed in gas phase, for each, using the Gaussian program package 03 Gauss. The three parameters of the exchange-correlation potential proposed by Becke with local and non-local correlations provided by Lee, Yang, and Parr (B3LYP functional) were selected with the basis set of triple zeta valence 6-311+G (d,p). Thermal contributions to the Gibbs free energy and other state functions were calculated at 298.15 K and 1 atm. The vibrational frequencies were scaled by a factor of 0.9381 for a better comparison with the experimental data.

Molecular Structure

Crystallographic Analysis

Figure 2:
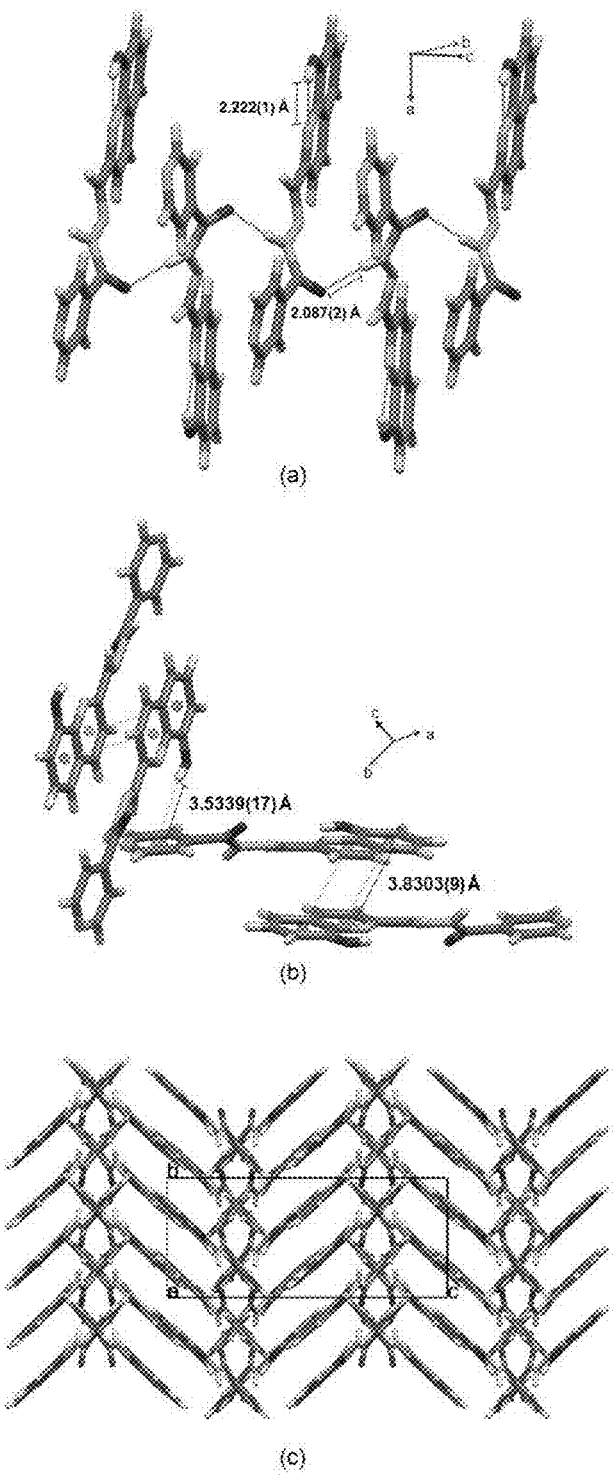

The main crystal parameters used, as well as data of information collected and structural refinement parameters are summarized in Table 1. INHHQ crystallizes in the orthorhombic system, space group Pbca. The asymmetric unit of INHHQ is shown in FIG. 1. The compound adopts an (E) configuration with respect to the C7=N3 bond of the hydrazonic group. The INHHQ molecule is almost planar in solid state (rms deviation=0.2701° for all atoms, except H) and shows an intramolecular H bond involving the phenolic hydroxyl and the quinolinic nitrogen group: the O1-H donor interacts with N4 [O1 . . . N4=2,689 Å] receptor. In this process, a pseudo five-membered ring is formed. The distances and bond angles (Table 2) are not significantly different from those observed in similar compounds. The crystal packing is maintained by intermolecular H bonds involving the carbonyl oxygen O2 (acceptor) of a molecule and the N2-H group of the following molecule [moderate N2 . . . O2$^i$=2,966 Å, symmetry codes: (i) −x+½, y−½, z], connecting the molecules of INHHQ in zigzag chains running parallel to the crystallographic b axis (FIG. 2a). The molecules in each chain are interconnected by cross-stacking π-π interactions involving the quinoline rings. The calculated centroid-centroid distance is equal to 3.8303(9) Å. The adjacent chains are interconnected by O1-H12 . . . π interactions (FIG. 2b), being the distance H12-centroid (N4-C8-C9-C10-C11-C12) of 3.5339(17) Å [symmetry code: −½+x, y, ½−z]. As a result of this last interaction, zigzag columns run parallel to the crystallographic axis a (FIG. 2c).

TABLE 1

Selected crystallographic data for INHHQ

| | |
|---|---|
| Empirical formula | $C_{16}H_{12}O_2N_4$ |
| Molecular weight | 292.30 |
| Collecting temperature | 293(2) K |
| Wave length | 0.71073 Å |
| Crystalline system | Orthorhombic |
| Space group | Pbca |
| Unit cell dimensions | a = 17.0761(4) Å |
| | b = 8.25480(10) Å |
| | c = 19.3549(4) Å |
| Cell volume | 2728.26(9) Å$^3$ |
| Z | 8 |
| ρ(calculated) | 1.423 g cm$^{-3}$ |
| Absorption coefficient | 0.098 mm$^{-1}$ |
| F(000) | 1216 |
| Crystal size utilized | 0.484 × 0.236 × 0.171 mm$^3$ |
| θ range used in collect | 2.94 a 27.48° |
| Index ranges | −22.19; −10.10; −25.23 |
| Collected reflections | 27142 |
| Unique | 3100 [R$_{(int)}$ = 0.1167] |
| Completeness to θ = 27.48° | 99.0% |
| Absorption correction | None |
| Refinement method | "Full-matrix least-squares on F$^2$" |
| Computational programs $^a$ | COLLECT, HKL Denzo and Scalepack, SHELXS-97, SHELXL-97 |
| Data/restraints/parameters | 3100/0/208 |
| Goodness-of-fit on F$^2$ | 1.042 |
| Final Rindexes [I > 2σ (I)] | R$_1$ = 0.0517, wR$_2$ = 0.1188 |
| R index (all data) | R$_1$ = 0.0968, wR$_2$ = 0.1427 |
| Largest diff. peak and hole | 0.198 and −0.234 e Å$^{-3}$ |

$^a$ Used for data collection, data processing, structure solution, and structure refinement, respectively.

TABLE 2

Main distances and bond angles, experimental and theoretical (Conf. 5), for INHHQ. The crystallographic identification scheme of the atoms was followed

| Distances (Å) | Experimental | Calculated | Distances (Å) | Experimental | Calculated |
|---|---|---|---|---|---|
| O2—C6 | 1.2268(18) | 1.211 | N4—C12 | 1.362(2) | 1.355 |
| N2—C6 | 1.345(2) | 1.388 | N3—C7 | 1.270(2) | 1.280 |
| N2—N3 | 1.3862(18) | 1.353 | O1—C13 | 1.358(2) | 1.351 |
| N4—C8 | 1.319(2) | 1.325 | N1—C1 | 1.333(2) | 1.335 |

| Angles (°) | | | Angles (°) | | |
|---|---|---|---|---|---|
| C6—N2—N3 | 118.44(13) | 120.9 | N2—C6—C5 | 115.04(13) | 114.0 |
| C8—N4—C12 | 117.83(13) | 118.6 | C1—N1—C2 | 116.20(15) | 117.2 |
| C7—N3—N2 | 115.54(13) | 117.4 | O1—C13—C12 | 118.65(15) | 118.8 |

TABLE 2-continued

Main distances and bond angles, experimental and theoretical (Conf. 5), for INHHQ. The crystallographic identification scheme of the atoms was followed

| Distances (Å) | Experimental | Calculated | Distances (Å) | Experimental | Calculated |
|---|---|---|---|---|---|
| Dihedral angles (°) | | | Dihedral angles (°) | | |
| C8—C7—N3—N2 | −177.63 | 179.7 | N3—N2—C6—C5 | −178.62 | −178.6 |
| C7—N3—N2—C6 | −163.79 | −175.4 | N2—C6—C5—C3 | 144.93 | −151.6 |

Figure 3:
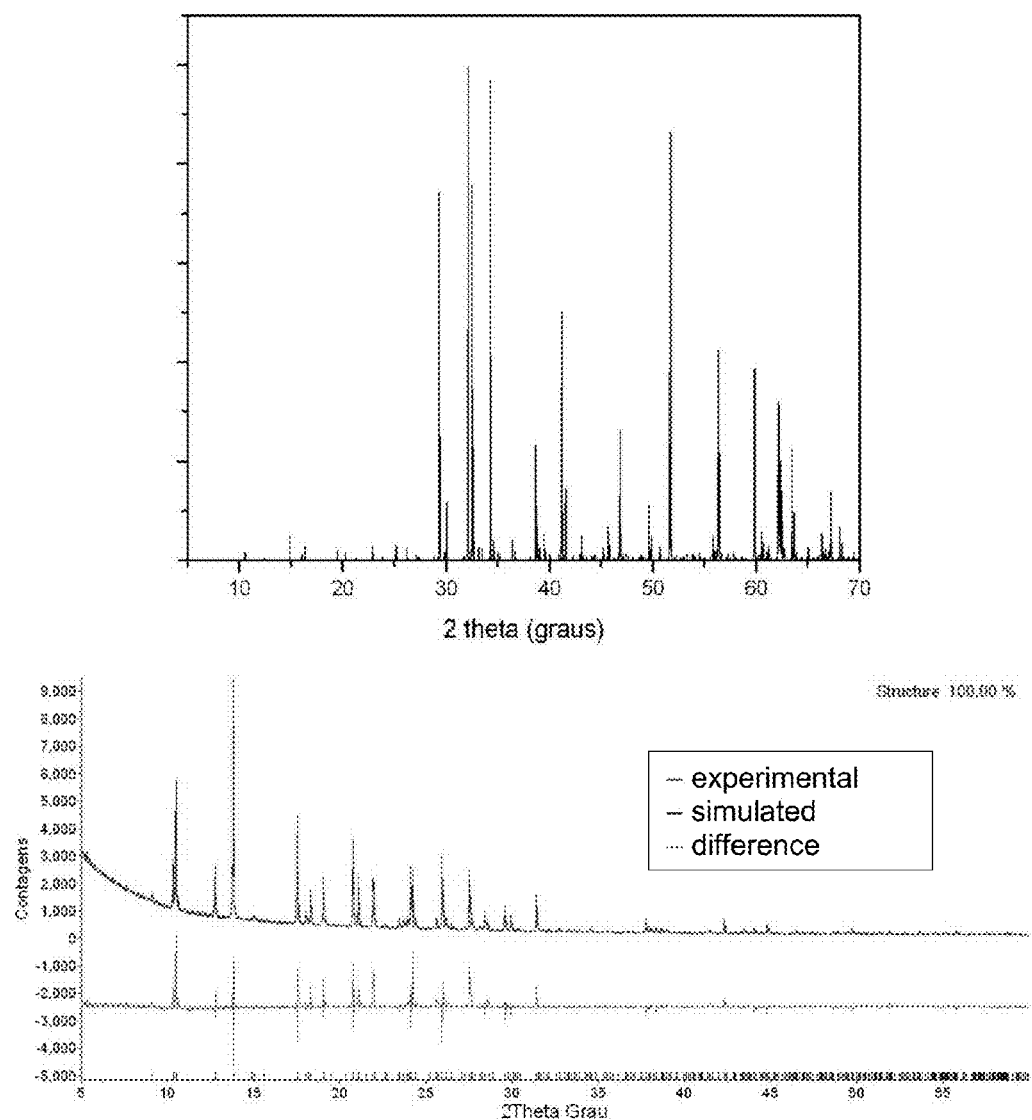
FIG. 3: Simulated and experimental X-ray diffractograms for INHHQ.

Moreover, an analysis of the INHHQ diffraction peaks was performed using Bragg-Brentano geometry (Table 3). The ultimate goal is to characterize, unambiguously, the obtained polymorph. The crystal structure-based simulated diffractogram in the range of 5<2θ<70°, was also calculated. FIG. 3 displays the superposition of the experimental (red) and simulated (blue) diffractograms.

TABLE 3

Information on the diffraction peaks of INHHQ for 2θ ranging from 10.5 to 70.5°

| Plane (h, k, l) | | | Multiplicity | Interplanar distance (Å) | 2 theta | Structure factor |
|---|---|---|---|---|---|---|
| h | k | l | m | d | (°) | $F^2$ |
| 1 | 0 | 0 | 2 | 8.34877 | 10.58783 | 1128.338 |
| 0 | 1 | 1 | 2 | 7.07920 | 12.49361 | 331.562 |
| 0 | 1 | 1 | 4 | 5.94931 | 14.87873 | 4309.398 |
| 1 | 0 | −2 | 2 | 5.93863 | 14.90564 | 3564.964 |
| 1 | −1 | −1 | 4 | 5.50433 | 16.08920 | 1058.563 |
| 0 | 0 | 2 | 2 | 5.48852 | 16.13588 | 185.920 |
| 1 | 1 | 0 | 4 | 5.39942 | 16.40394 | 3734.208 |
| 1 | −1 | −2 | 4 | 4.54974 | 19.49495 | 3562.456 |
| 1 | 1 | 1 | 4 | 4.37713 | 20.27167 | 81.922 |
| 2 | 0 | −2 | 2 | 4.37659 | 20.27421 | 2544.993 |
| 0 | 1 | 2 | 4 | 4.33757 | 20.45853 | 131.263 |
| 2 | 0 | 0 | 2 | 4.17439 | 21.26742 | 743.827 |
| 2 | −1 | −1 | 4 | 3.87923 | 22.90666 | 5227.304 |
| 1 | 0 | 2 | 2 | 3.87110 | 22.95541 | 2615.373 |
| 2 | −1 | −2 | 4 | 3.72262 | 23.88427 | 1558.836 |
| 2 | 1 | 0 | 4 | 3.59579 | 24.73979 | 177.345 |
| 0 | 2 | 0 | 2 | 3.53960 | 25.13890 | 1609.181 |
| 1 | −1 | −3 | 4 | 3.53090 | 25.20189 | 4821.653 |
| 1 | 1 | 2 | 4 | 3.39646 | 26.21681 | 4682.200 |
| 0 | 2 | 1 | 4 | 3.36879 | 26.43604 | 783.016 |
| 1 | −2 | −1 | 4 | 3.28146 | 27.15290 | 1838.082 |
| 1 | 2 | 0 | 4 | 3.25881 | 27.34522 | 1594.341 |
| 2 | −1 | −3 | 4 | 3.25355 | 27.39035 | 1187.558 |
| 0 | 1 | 3 | 4 | 3.25049 | 27.41659 | 1027.571 |
| 3 | 0 | −2 | 2 | 3.08971 | 28.87348 | 81.686 |
| 2 | 1 | 1 | 4 | 3.08859 | 28.88417 | 2178.500 |
| 1 | −2 | −2 | 4 | 3.04049 | 29.35123 | 126085.008 |
| 1 | 0 | −4 | 2 | 3.03231 | 29.43221 | 46210.547 |
| 1 | 2 | 1 | 4 | 2.98732 | 29.88574 | 3959.848 |
| 0 | 2 | 2 | 4 | 2.97465 | 30.01599 | 23814.010 |
| 2 | 0 | −4 | 2 | 2.96931 | 30.07124 | 20257.656 |
| 3 | −1 | −2 | 4 | 2.83175 | 31.56923 | 1316.031 |
| 2 | −2 | −1 | 4 | 2.81367 | 31.77739 | 2147.033 |
| 3 | −1 | −1 | 4 | 2.78865 | 32.07025 | 962.328 |
| 1 | −1 | −4 | 4 | 2.78737 | 32.08534 | 5017.017 |
| 2 | 0 | 2 | 2 | 2.78466 | 32.11737 | 5954.872 |
| 3 | 0 | 0 | 2 | 2.78292 | 32.13796 | 198029.766 |
| 2 | −2 | −2 | 4 | 2.75217 | 32.50702 | 166846.703 |
| 0 | 0 | 4 | 2 | 2.74426 | 32.60332 | 78569.977 |
| 2 | −1 | −4 | 4 | 2.73820 | 32.67747 | 7683.784 |
| 2 | 2 | 0 | 4 | 2.69971 | 33.15667 | 5524.309 |
| 3 | −1 | −3 | 4 | 2.69759 | 33.18355 | 5725.885 |
| 1 | 1 | 3 | 4 | 2.69411 | 33.22766 | 3144.983 |
| 1 | −2 | −3 | 4 | 2.67192 | 33.51166 | 5080.103 |
| 1 | 2 | 2 | 4 | 2.61222 | 34.30092 | 184684.922 |
| 3 | 0 | −4 | 2 | 2.61018 | 34.32857 | 75081.414 |
| 2 | 1 | 2 | 4 | 2.59139 | 34.58541 | 10269.332 |
| 3 | 1 | 0 | 4 | 2.58999 | 34.60470 | 3123.402 |

TABLE 3-continued

Information on the diffraction peaks of INHHQ for 2θ ranging from 10.5 to 70.5°

| Plane (h, k, l) | | | Multiplicity | Interplanar distance (Å) | 2 theta | Structure factor |
|---|---|---|---|---|---|---|
| h | k | l | m | d | (°) | $F^2$ |
| 0 | 1 | 4 | 4 | 2.55873 | 35.04100 | 3632.206 |
| 2 | −2 | −3 | 4 | 2.54551 | 35.22898 | 128.840 |
| 0 | 2 | 3 | 4 | 2.54404 | 35.24991 | 2518.650 |
| 2 | 2 | 1 | 4 | 2.46414 | 36.43237 | 9364.604 |
| 3 | −1 | −4 | 4 | 2.44902 | 36.66531 | 6171.995 |
| 0 | 3 | 0 | 2 | 2.35973 | 38.10499 | 2742.504 |
| 3 | −2 | −2 | 4 | 2.32767 | 38.65065 | 49774.492 |
| 1 | 0 | 4 | 2 | 2.32176 | 38.75283 | 27728.582 |
| 4 | 0 | −2 | 2 | 2.31874 | 38.80530 | 8126.180 |
| 3 | 1 | 1 | 4 | 2.31772 | 38.82317 | 7422.130 |
| 0 | 3 | 1 | 4 | 2.30703 | 39.01032 | 1802.321 |
| 3 | −2 | −1 | 4 | 2.30355 | 39.07167 | 4033.272 |
| 1 | −2 | −4 | 4 | 2.30283 | 39.08438 | 4588.360 |
| 2 | −1 | −5 | 4 | 2.30097 | 39.11728 | 4454.373 |
| 1 | −3 | −1 | 4 | 2.27839 | 39.52090 | 11520.123 |
| 2 | −2 | −4 | 4 | 2.27487 | 39.58469 | 7746.600 |
| 1 | −1 | −5 | 4 | 2.27151 | 39.64563 | 598.446 |
| 1 | 3 | 0 | 4 | 2.27077 | 39.65907 | 2802.268 |
| 3 | −2 | −3 | 4 | 2.25142 | 40.01449 | 3656.189 |
| 1 | 2 | 3 | 4 | 2.24939 | 40.05204 | 2882.448 |
| 1 | 1 | 4 | 4 | 2.20614 | 40.87197 | 4367.143 |
| 4 | −1 | −2 | 4 | 2.20355 | 40.92216 | 1606.162 |
| 1 | −3 | −2 | 4 | 2.19295 | 41.12888 | 5896.017 |
| 2 | 2 | 2 | 4 | 2.18856 | 41.21509 | 90978.344 |
| 4 | 0 | −4 | 2 | 2.18829 | 41.22042 | 43250.957 |
| 3 | 2 | 0 | 4 | 2.18772 | 41.23171 | 13279.063 |
| 4 | −1 | −3 | 4 | 2.18705 | 41.24487 | 37423.781 |
| 2 | 1 | 3 | 4 | 2.18427 | 41.29979 | 20309.209 |
| 1 | 3 | 1 | 4 | 2.17275 | 41.52890 | 27249.758 |
| 0 | 2 | 4 | 4 | 2.16879 | 41.60831 | 20608.090 |
| 3 | −1 | −5 | 4 | 2.16859 | 41.61228 | 15481.041 |
| 0 | 3 | 2 | 4 | 2.16786 | 41.62688 | 3233.373 |
| 4 | −1 | −1 | 4 | 2.13480 | 42.30230 | 2642.791 |
| 3 | 0 | 2 | 2 | 2.13258 | 42.34844 | 20.261 |
| 2 | −3 | −1 | 4 | 2.10312 | 42.97079 | 2666.499 |
| 3 | −2 | −4 | 4 | 2.10076 | 43.02150 | 1828.689 |
| 0 | 1 | 5 | 4 | 2.09689 | 43.10495 | 17605.400 |
| 4 | −1 | −4 | 4 | 2.09069 | 43.23919 | 2405.904 |
| 4 | 0 | 0 | 2 | 2.08719 | 43.31522 | 1974.789 |
| 2 | −3 | −2 | 4 | 2.07706 | 43.53728 | 2901.627 |
| 2 | 3 | 0 | 4 | 2.05423 | 44.04625 | 3037.751 |
| 3 | 1 | 2 | 4 | 2.04194 | 44.32549 | 1874.683 |
| 1 | −3 | −3 | 4 | 2.04191 | 44.32613 | 1474.088 |
| 2 | 0 | −6 | 2 | 2.03690 | 44.44102 | 2853.471 |
| 3 | 2 | 1 | 4 | 2.01612 | 44.92393 | 1408.763 |
| 1 | 3 | 2 | 4 | 2.01489 | 44.95273 | 793.879 |
| 2 | −2 | −5 | 4 | 2.00506 | 45.18528 | 8021.569 |
| 4 | 1 | 0 | 4 | 2.00199 | 45.25840 | 3930.259 |
| 1 | −2 | −5 | 4 | 1.98548 | 45.65592 | 1014.055 |
| 2 | −3 | −3 | 4 | 1.98380 | 45.69690 | 16302.775 |
| 0 | 3 | 3 | 4 | 1.98310 | 45.71378 | 11086.845 |
| 3 | 0 | −6 | 2 | 1.97954 | 45.80066 | 5989.497 |
| 1 | 0 | −6 | 2 | 1.97817 | 45.83434 | 9677.354 |
| 2 | −1 | −6 | 4 | 1.95748 | 46.34679 | 2033.378 |
| 2 | 3 | 1 | 4 | 1.94455 | 46.67316 | 3814.112 |
| 4 | −1 | −5 | 4 | 1.94222 | 46.73259 | 2465.540 |
| 1 | 2 | 4 | 4 | 1.94138 | 46.75385 | 1044.347 |

TABLE 3-continued

Information on the diffraction peaks of INHHQ for 2θ ranging from 10.5 to 70.5°

| Plane (h, k, l) | | | Multiplicity | Interplanar distance (Å) | 2 theta | Structure factor |
|---|---|---|---|---|---|---|
| h | k | l | m | d | (°) | F² |
| 4 | −2 | −2 | 4 | 1.93962 | 46.79894 | 71647.414 |
| 2 | 0 | 4 | 2 | 1.93555 | 46.90307 | 22593.117 |
| 4 | −2 | −3 | 4 | 1.92834 | 47.08917 | 2359.305 |
| 2 | 2 | 3 | 4 | 1.92643 | 47.13862 | 3496.081 |
| 3 | −2 | −5 | 4 | 1.91564 | 47.42022 | 3565.626 |
| 3 | −1 | −6 | 4 | 1.90641 | 47.66401 | 3852.061 |
| 1 | −1 | −6 | 4 | 1.90518 | 47.69668 | 126.165 |
| 4 | −2 | −1 | 4 | 1.89223 | 48.04363 | 2471.013 |
| 3 | −3 | −2 | 4 | 1.87535 | 48.50388 | 728.923 |
| 2 | 1 | 4 | 4 | 1.86703 | 48.73407 | 2582.125 |
| 0 | 2 | 5 | 4 | 1.86568 | 48.77150 | 687.112 |
| 3 | −3 | −1 | 4 | 1.86266 | 48.85561 | 371.683 |
| 1 | −3 | −4 | 4 | 1.86228 | 48.86626 | 3642.781 |
| 4 | −2 | −4 | 4 | 1.86131 | 48.89351 | 961.915 |
| 1 | 1 | 5 | 4 | 1.85776 | 48.99309 | 2897.553 |
| 2 | −3 | −4 | 4 | 1.84740 | 49.28595 | 2366.935 |
| 5 | 0 | −2 | 2 | 1.83827 | 49.54725 | 191.546 |
| 4 | 1 | 1 | 4 | 1.83748 | 49.56990 | 893.848 |
| 3 | −3 | −3 | 4 | 1.83478 | 49.64793 | 34517.039 |
| 1 | 3 | 3 | 4 | 1.83368 | 49.67962 | 3586.474 |
| 4 | 0 | −6 | 2 | 1.83168 | 49.73747 | 1341.276 |
| 0 | 0 | 6 | 2 | 1.82951 | 49.80075 | 5427.721 |
| 5 | 0 | −4 | 2 | 1.82704 | 49.87241 | 2611.138 |
| 3 | 2 | 2 | 4 | 1.82666 | 49.88361 | 15035.101 |
| 2 | 3 | 2 | 4 | 1.80028 | 50.66584 | 852.734 |
| 3 | 3 | 0 | 4 | 1.79981 | 50.68000 | 7635.262 |
| 4 | 2 | 0 | 4 | 1.79790 | 50.73774 | 31.252 |
| 5 | −1 | −3 | 4 | 1.79778 | 50.74113 | 3492.466 |
| 3 | 1 | 3 | 4 | 1.79572 | 50.80350 | 1004.864 |
| 0 | 3 | 4 | 4 | 1.78922 | 51.00132 | 203.157 |
| 5 | −1 | −2 | 4 | 1.77926 | 51.30747 | 668.832 |
| 4 | −1 | −6 | 4 | 1.77329 | 51.49295 | 1637.459 |
| 0 | 1 | 6 | 4 | 1.77131 | 51.55465 | 738.791 |
| 0 | 4 | 0 | 2 | 1.76980 | 51.60187 | 118322.898 |
| 5 | −1 | −4 | 4 | 1.76908 | 51.62454 | 2002.556 |
| 2 | −2 | −6 | 4 | 1.76545 | 51.73845 | 267467.688 |
| 4 | −2 | −5 | 4 | 1.75423 | 52.09423 | 1767.949 |
| 3 | −3 | −4 | 4 | 1.75045 | 52.21513 | 447.095 |
| 0 | 4 | 1 | 4 | 1.74724 | 52.31836 | 2620.549 |
| 1 | −4 | −1 | 4 | 1.73470 | 52.72556 | 2457.296 |
| 1 | 4 | 0 | 4 | 1.73133 | 52.83614 | 1390.317 |
| 3 | −2 | −6 | 4 | 1.72771 | 52.95524 | 624.514 |
| 1 | −2 | −6 | 4 | 1.72680 | 52.98560 | 2870.138 |
| 5 | −1 | −1 | 4 | 1.71763 | 53.29042 | 3992.833 |
| 4 | 0 | 2 | 2 | 1.71625 | 53.33669 | 171.427 |
| 3 | 3 | 1 | 4 | 1.70057 | 53.86813 | 4463.794 |
| 5 | −1 | −5 | 4 | 1.69944 | 53.90672 | 1663.483 |
| 2 | 2 | 4 | 4 | 1.69823 | 53.94829 | 3506.858 |
| 1 | −4 | −2 | 4 | 1.69608 | 54.02211 | 2307.989 |
| 2 | −3 | −5 | 4 | 1.69369 | 54.09682 | 2349.578 |
| 1 | 2 | 5 | 4 | 1.69125 | 54.18921 | 1409.942 |
| 2 | −1 | −7 | 4 | 1.69108 | 54.19489 | 787.935 |
| 1 | 4 | 1 | 4 | 1.68669 | 54.34788 | 882.257 |
| 0 | 4 | 2 | 4 | 1.68440 | 54.42786 | 182.510 |
| 1 | −3 | −5 | 4 | 1.68206 | 54.50961 | 4158.873 |
| 3 | −1 | −7 | 4 | 1.68013 | 54.57753 | 2978.968 |
| 4 | 2 | 1 | 4 | 1.67591 | 54.72649 | 1026.918 |
| 5 | 0 | 0 | 2 | 1.66975 | 54.94516 | 2190.528 |
| 4 | 1 | 2 | 4 | 1.66794 | 55.01012 | 1131.238 |
| 1 | 3 | 4 | 4 | 1.65500 | 55.47716 | 297.480 |
| 4 | −3 | −2 | 4 | 1.65390 | 55.51703 | 92.102 |
| 2 | −4 | −1 | 4 | 1.65348 | 55.53225 | 2628.066 |
| 4 | −3 | −3 | 4 | 1.64689 | 55.77391 | 1703.457 |
| 2 | 3 | 3 | 4 | 1.64570 | 55.81771 | 14933.787 |
| 5 | −2 | −3 | 4 | 1.64562 | 55.82063 | 904.931 |
| 5 | 0 | −6 | 2 | 1.64485 | 55.84915 | 11045.036 |
| 3 | 2 | 3 | 4 | 1.64404 | 55.87900 | 537.543 |
| 1 | 0 | 6 | 2 | 1.64248 | 55.93667 | 4104.017 |
| 2 | −4 | −2 | 4 | 1.64073 | 56.00177 | 6555.738 |
| 3 | −3 | −5 | 4 | 1.63896 | 56.06742 | 3117.231 |
| 1 | −1 | −7 | 4 | 1.63562 | 56.19224 | 7479.478 |
| 5 | −2 | −2 | 4 | 1.63138 | 56.35117 | 139974.406 |
| 2 | 4 | 0 | 4 | 1.62941 | 56.42557 | 2336.839 |
| 3 | 0 | 4 | 2 | 1.62858 | 56.45687 | 79060.617 |
| 4 | −2 | −6 | 4 | 1.62677 | 56.52512 | 231.031 |
| 0 | 2 | 6 | 4 | 1.62525 | 56.58301 | 200.360 |
| 5 | 1 | 0 | 4 | 1.62516 | 56.58630 | 1372.377 |
| 4 | −3 | −1 | 4 | 1.62423 | 56.62165 | 941.537 |
| 5 | −2 | −4 | 4 | 1.62352 | 56.64860 | 977.446 |
| 1 | −4 | −3 | 4 | 1.62324 | 56.65939 | 3828.351 |
| 2 | 1 | 5 | 4 | 1.62060 | 56.76011 | 661.635 |
| 1 | 4 | 2 | 4 | 1.60956 | 57.18482 | 2848.325 |
| 0 | 3 | 5 | 4 | 1.60734 | 57.27112 | 4687.052 |
| 4 | −1 | −7 | 4 | 1.60639 | 57.30817 | 785.019 |
| 4 | −3 | −4 | 4 | 1.60455 | 57.38024 | 979.594 |
| 5 | −1 | −6 | 4 | 1.60217 | 57.47322 | 229.132 |
| 1 | 1 | 6 | 4 | 1.59998 | 57.55912 | 756.968 |
| 2 | −4 | −3 | 4 | 1.59358 | 57.81228 | 6432.516 |
| 0 | 4 | 3 | 4 | 1.59322 | 57.82655 | 993.033 |
| 3 | 1 | 4 | 4 | 1.58712 | 58.06987 | 1480.846 |
| 5 | −2 | −1 | 4 | 1.58349 | 58.21592 | 1232.501 |
| 3 | 3 | 2 | 4 | 1.58219 | 58.26825 | 878.980 |
| 2 | 4 | 1 | 4 | 1.57302 | 58.64091 | 2737.882 |
| 5 | −2 | −5 | 4 | 1.56920 | 58.79766 | 1757.640 |
| 4 | 3 | 0 | 4 | 1.56339 | 59.03785 | 1224.589 |
| 2 | −2 | −7 | 4 | 1.56261 | 59.07000 | 858.527 |
| 3 | −2 | −7 | 4 | 1.55396 | 59.43196 | 388.934 |
| 6 | 0 | −4 | 2 | 1.54485 | 59.81773 | 40226.578 |
| 4 | 2 | 2 | 4 | 1.54429 | 59.84161 | 132527.313 |
| 2 | −3 | −6 | 4 | 1.54191 | 59.94356 | 919.952 |
| 3 | −4 | −2 | 4 | 1.53571 | 60.21080 | 3337.484 |
| 4 | −3 | −5 | 4 | 1.53442 | 60.26657 | 2142.301 |
| 0 | 1 | 7 | 4 | 1.53103 | 60.41363 | 4066.389 |
| 3 | −4 | −1 | 4 | 1.52872 | 60.51473 | 530.741 |
| 1 | −4 | −4 | 4 | 1.52851 | 60.52394 | 23281.965 |
| 3 | 0 | −8 | 2 | 1.52498 | 60.67867 | 13248.033 |
| 2 | −4 | −4 | 4 | 1.52025 | 60.88755 | 1880.706 |
| 1 | −2 | −7 | 4 | 1.51854 | 60.96338 | 1753.461 |
| 6 | 0 | −2 | 2 | 1.51698 | 61.03271 | 2012.546 |
| 3 | −3 | −6 | 4 | 1.51658 | 61.05053 | 1466.016 |
| 5 | 1 | 1 | 4 | 1.51638 | 61.05931 | 161.170 |
| 2 | 0 | −8 | 2 | 1.51616 | 61.06934 | 3710.299 |
| 1 | −3 | −6 | 4 | 1.51596 | 61.07813 | 2665.123 |
| 3 | −4 | −3 | 4 | 1.51319 | 61.20197 | 419.151 |
| 1 | 4 | 3 | 4 | 1.51257 | 61.22953 | 10115.472 |
| 6 | −1 | −3 | 4 | 1.51024 | 61.33418 | 363.616 |
| 5 | 2 | 0 | 4 | 1.51016 | 61.33806 | 617.463 |
| 6 | −1 | −4 | 4 | 1.50933 | 61.37515 | 989.558 |
| 4 | 1 | 3 | 4 | 1.50872 | 61.40297 | 297.840 |
| 2 | 2 | 5 | 4 | 1.50649 | 61.50344 | 588.937 |
| 2 | 3 | 4 | 4 | 1.49652 | 61.95818 | 590.113 |
| 4 | −2 | −7 | 4 | 1.49506 | 62.02536 | 423.413 |
| 2 | 4 | 2 | 4 | 1.49366 | 62.09007 | 106.506 |
| 3 | 4 | 0 | 4 | 1.49339 | 62.10246 | 123565.250 |
| 1 | 3 | 5 | 4 | 1.49174 | 62.17898 | 478.546 |
| 5 | −2 | −6 | 4 | 1.49166 | 62.18267 | 105324.078 |
| 5 | −1 | −7 | 4 | 1.49157 | 62.18692 | 1581.715 |
| 3 | −1 | −8 | 4 | 1.49078 | 62.22328 | 974.226 |
| 1 | 2 | 6 | 4 | 1.48989 | 62.26457 | 134633.219 |
| 0 | 4 | 4 | 4 | 1.48733 | 62.38401 | 83526.117 |
| 4 | 0 | −8 | 2 | 1.48466 | 62.50882 | 50996.125 |
| 6 | −1 | −2 | 4 | 1.48331 | 62.57221 | 539.855 |
| 2 | −1 | −8 | 4 | 1.48254 | 62.60831 | 1032.783 |
| 4 | 3 | 1 | 4 | 1.48118 | 62.67218 | 6016.078 |
| 6 | −1 | −5 | 4 | 1.48072 | 62.69367 | 7655.220 |
| 3 | 2 | 4 | 4 | 1.47949 | 62.75186 | 5174.257 |
| 3 | −4 | −4 | 4 | 1.46483 | 63.45251 | 92852.609 |
| 1 | 0 | −8 | 2 | 1.46062 | 63.65703 | 34382.762 |
| 5 | −3 | −3 | 4 | 1.46015 | 63.67986 | 19231.883 |
| 3 | 3 | 3 | 4 | 1.45904 | 63.73375 | 2083.547 |
| 6 | 0 | −6 | 2 | 1.45886 | 63.74255 | 104.403 |
| 2 | 0 | 6 | 2 | 1.45666 | 63.85023 | 5589.541 |
| 4 | −1 | −8 | 4 | 1.45305 | 64.02798 | 501.111 |
| 5 | −3 | −2 | 4 | 1.45017 | 64.17003 | 1181.973 |

TABLE 3-continued

Information on the diffraction peaks of INHHQ for 2θ ranging from 10.5 to 70.5°

| Plane (h, k, l) | | | Multiplicity | Interplanar distance (Å) | 2 theta | Structure factor |
|---|---|---|---|---|---|---|
| h | k | l | m | d | (°) | F² |
| 4 | −3 | −6 | 4 | 1.44693 | 64.33096 | 2199.269 |
| 0 | 3 | 6 | 4 | 1.44586 | 64.38455 | 3392.815 |
| 5 | −3 | −4 | 4 | 1.44464 | 64.44527 | 603.990 |
| 3 | 4 | 1 | 4 | 1.43522 | 64.91979 | 856.294 |
| 0 | 2 | 7 | 4 | 1.43374 | 64.99512 | 3941.112 |
| 6 | −1 | −1 | 4 | 1.43271 | 65.04772 | 9958.013 |
| 5 | 0 | 2 | 2 | 1.43178 | 65.09530 | 464.878 |
| 2 | −4 | −5 | 4 | 1.43122 | 65.12385 | 1343.613 |
| 1 | −1 | −8 | 4 | 1.43049 | 65.16140 | 2849.458 |
| 6 | −1 | −6 | 4 | 1.42884 | 65.24586 | 1632.203 |
| 2 | 1 | 6 | 4 | 1.42677 | 65.35220 | 113.830 |
| 1 | −4 | −5 | 4 | 1.42405 | 65.49281 | 2715.529 |
| 5 | 2 | 1 | 4 | 1.42169 | 65.61512 | 2686.276 |
| 6 | −2 | −3 | 4 | 1.41663 | 65.87928 | 845.347 |
| 5 | −3 | −1 | 4 | 1.41622 | 65.90063 | 1809.560 |
| 6 | −2 | −4 | 4 | 1.41588 | 65.91867 | 654.705 |
| 0 | 5 | 0 | 2 | 1.41584 | 65.92052 | 1197.549 |
| 4 | 2 | 3 | 4 | 1.41537 | 65.94542 | 244.526 |
| 3 | 1 | 5 | 4 | 1.41356 | 66.04055 | 4426.744 |
| 1 | 4 | 4 | 4 | 1.40751 | 66.36081 | 21200.830 |
| 4 | −4 | −2 | 4 | 1.40684 | 66.39668 | 396.245 |
| 5 | −3 | −5 | 4 | 1.40597 | 66.44291 | 29.975 |
| 5 | 0 | −8 | 2 | 1.40574 | 66.45520 | 3142.987 |
| 0 | 5 | 1 | 4 | 1.40421 | 66.53712 | 7893.484 |
| 5 | 1 | 2 | 4 | 1.40336 | 66.58237 | 970.894 |
| 1 | 1 | 7 | 4 | 1.40288 | 66.60856 | 170.244 |
| 4 | −4 | −3 | 4 | 1.40251 | 66.62790 | 1310.150 |
| 2 | 4 | 3 | 4 | 1.40178 | 66.66737 | 2531.638 |
| 2 | −3 | −7 | 4 | 1.40123 | 66.69715 | 8505.064 |
| 5 | −2 | −7 | 4 | 1.40118 | 66.69978 | 401.337 |
| 3 | −2 | −8 | 4 | 1.40053 | 66.73479 | 5147.162 |
| 1 | −5 | −1 | 4 | 1.39767 | 66.88894 | 1543.957 |
| 3 | −4 | −5 | 4 | 1.39761 | 66.89248 | 1963.978 |
| 1 | 5 | 0 | 4 | 1.39591 | 66.98464 | 1123.055 |
| 3 | −3 | −7 | 4 | 1.39498 | 67.03543 | 1584.166 |
| 6 | −2 | −2 | 4 | 1.39432 | 67.07096 | 6423.831 |
| 2 | −2 | −8 | 4 | 1.39368 | 67.10576 | 2221.480 |
| 4 | 0 | 4 | 2 | 1.39233 | 67.17963 | 9756.798 |
| 6 | −2 | −5 | 4 | 1.39218 | 67.18803 | 123.361 |
| 6 | 0 | 0 | 2 | 1.39146 | 67.22715 | 61458.719 |
| 4 | −4 | −1 | 4 | 1.38844 | 67.39312 | 1208.544 |
| 4 | 3 | 2 | 4 | 1.38797 | 67.41877 | 146.200 |
| 5 | −1 | −8 | 4 | 1.37882 | 67.92709 | 1203.279 |
| 0 | 4 | 5 | 4 | 1.37785 | 67.98154 | 710.651 |
| 1 | −5 | −2 | 4 | 1.37724 | 68.01559 | 3062.095 |
| 4 | −4 | −4 | 4 | 1.37608 | 68.08057 | 27359.787 |
| 1 | 5 | 1 | 4 | 1.37219 | 68.30019 | 694.557 |
| 0 | 0 | 8 | 2 | 1.37213 | 68.30382 | 15200.482 |
| 0 | 5 | 2 | 4 | 1.37096 | 68.37016 | 828.054 |
| 1 | −3 | −7 | 4 | 1.36918 | 68.47118 | 3214.390 |
| 4 | −2 | −8 | 4 | 1.36910 | 68.47589 | 45.553 |
| 4 | 1 | 4 | 4 | 1.36616 | 68.64389 | 519.685 |
| 6 | 1 | 0 | 4 | 1.36534 | 68.69093 | 1607.419 |
| 5 | 3 | 0 | 4 | 1.36303 | 68.82355 | 2112.606 |
| 3 | 4 | 2 | 4 | 1.36190 | 68.88850 | 1753.492 |
| 6 | −1 | −7 | 4 | 1.36065 | 68.96085 | 2649.621 |
| 2 | 3 | 5 | 4 | 1.36033 | 68.97921 | 2510.422 |
| 2 | −5 | −1 | 4 | 1.35414 | 69.33989 | 3657.629 |
| 6 | −2 | −1 | 4 | 1.35205 | 69.46230 | 243.801 |
| 4 | −3 | −7 | 4 | 1.35190 | 69.47100 | 6915.945 |
| 1 | −2 | −8 | 4 | 1.35018 | 69.57237 | 1099.760 |
| 4 | 4 | 0 | 4 | 1.34986 | 69.59140 | 705.399 |
| 5 | −3 | −6 | 4 | 1.34938 | 69.61938 | 756.755 |
| 6 | −2 | −6 | 4 | 1.34879 | 69.65417 | 2227.248 |
| 1 | 3 | 6 | 4 | 1.34807 | 69.69667 | 318.911 |
| 2 | −5 | −2 | 4 | 1.34710 | 69.75419 | 61.678 |
| 0 | 1 | 8 | 4 | 1.34706 | 69.75684 | 1471.690 |
| 2 | 2 | 6 | 4 | 1.34705 | 69.75717 | 576.139 |
| 2 | 5 | 0 | 4 | 1.34082 | 70.12915 | 2349.962 |
| 3 | 3 | 4 | 4 | 1.34035 | 70.15689 | 35.647 |
| 1 | −5 | −3 | 4 | 1.33737 | 70.33644 | 2229.274 |
| 2 | −4 | −6 | 4 | 1.33596 | 70.42175 | 3337.051 |
| 3 | 2 | 5 | 4 | 1.33592 | 70.42439 | 156.499 |

Gas-Phase DFT Calculations

The INHHQ structure was optimized in gas phase, using the DFT methodology, level of theory B3LYP/6-311+G (d,p).

As described above, a total of 5 conformations with the smallest PM3 energy differences were selected to perform a DFT optimization and frequency calculations. Cis-trans isomerism was contemplated in this treatment. Energy values found for each of these structures indicated that there are, in fact, only 3 different conformations. Conf. 5 is the one with the lowest free energy (ΔG) when compared to the other conformations. However, the energy differences between the structures are not appreciable, especially between the Conf. 1/2 with respect to the Conf. 5 (only 0.06 kcal mol$^{-1}$), indicating that, indeed, all five conformations are possible, particularly Conf. 5. This last one was chosen for further deeper studies.

Figure 4:
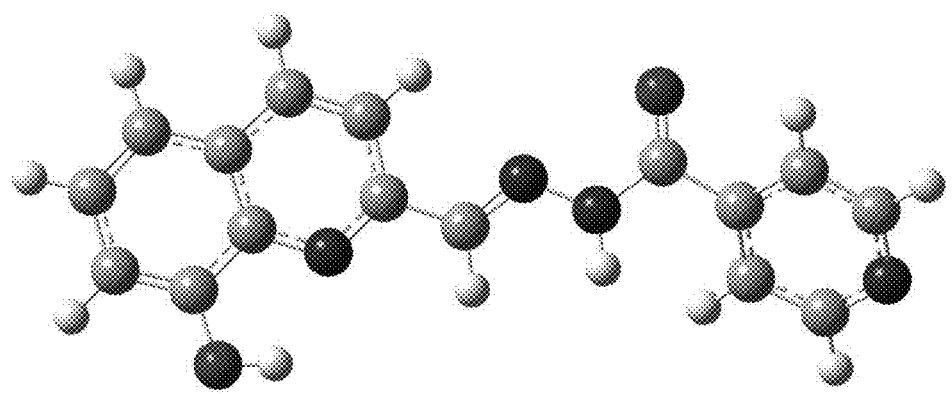
FIG. 4: Most stable calculated structure in the gas-phase (Conf. 5). Level of theory: B3LYP/6-311+G (d,p)

It is shown (Table 2) that there is excellent agreement between the structural parameters found in the calculations (Conf. 5) and the refined X-ray structure and that, in turn, there is no significant difference between FIGS. 1 and 4. Crystallography shows that the phenolic hydrogen points in the direction of the quinolinic nitrogen, since a connection involving these H atoms is formed, producing a 2.691 Å donor-acceptor distance, in perfect agreement with the X-ray data (O1 . . . N4=2.689 Å).

Vibrational Analyses

Figure 5:
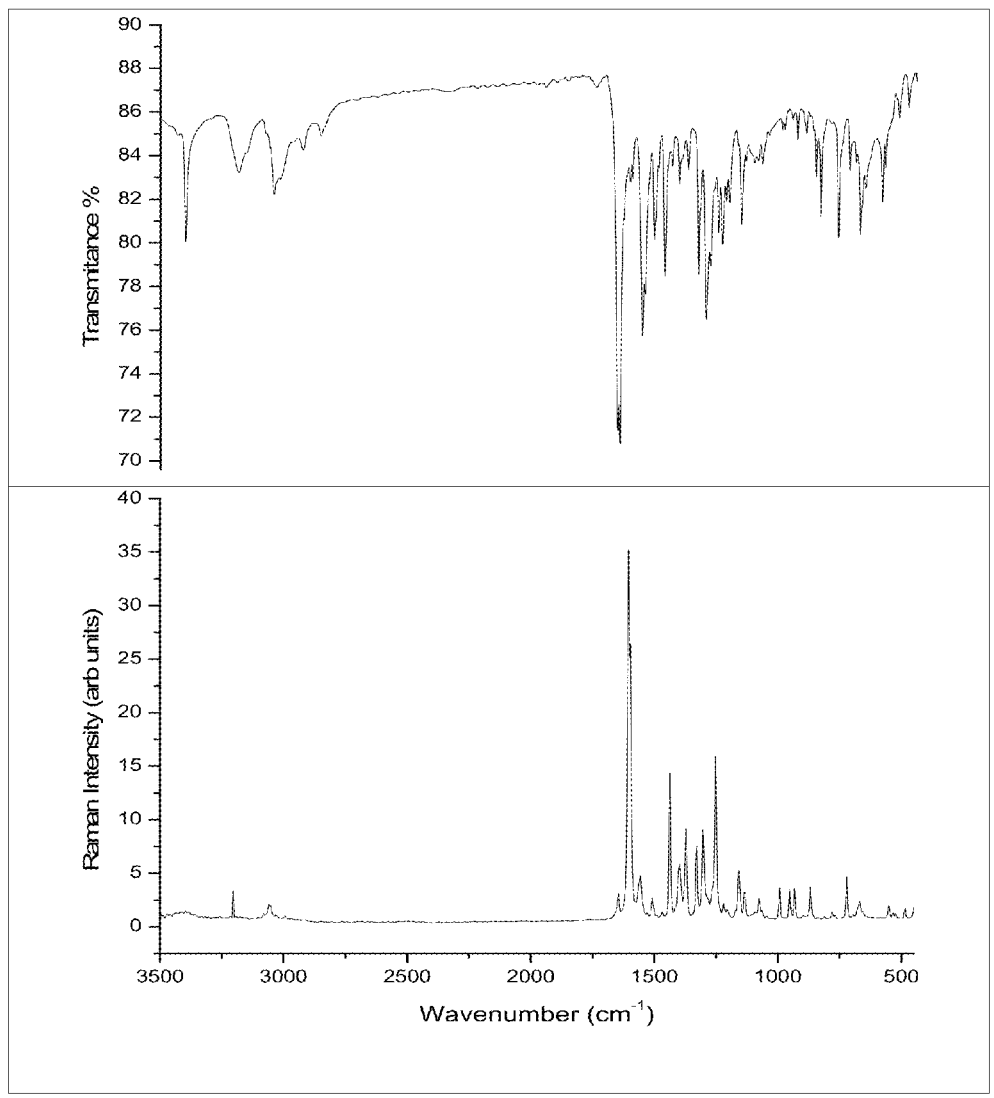
FIG. 5: FTIR (above) and Raman (below) spectra of INHHQ.
Figure 6:
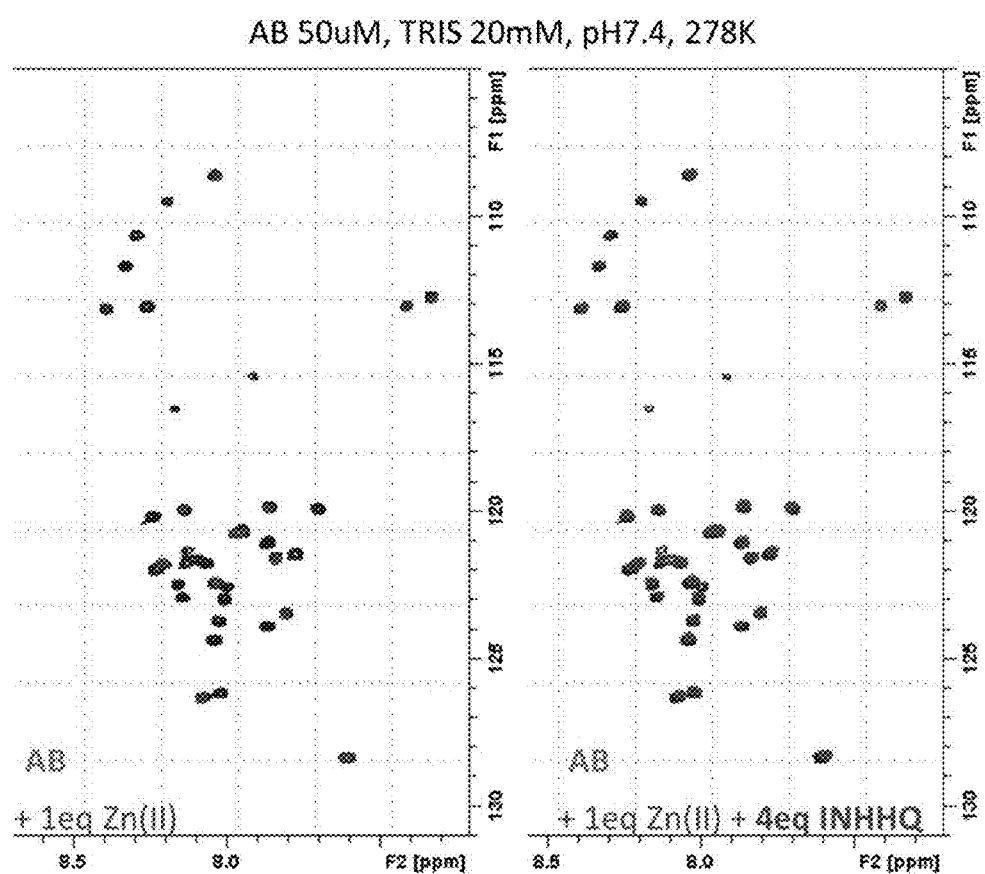
FIG. 6: 2D $^1H\times^{15}N$ HSQC contour plots showing that the addition of INHHQ (4 eq.) to a mixture containing the β-amyloid peptide and Zn(II) (1 eq.) leads to a partial intensity recovery for all Aβ signals, which can be considered as an indicative that the hydrazone INHHQ weakens Zn(II)-Aβ interactions.
Figure 7:
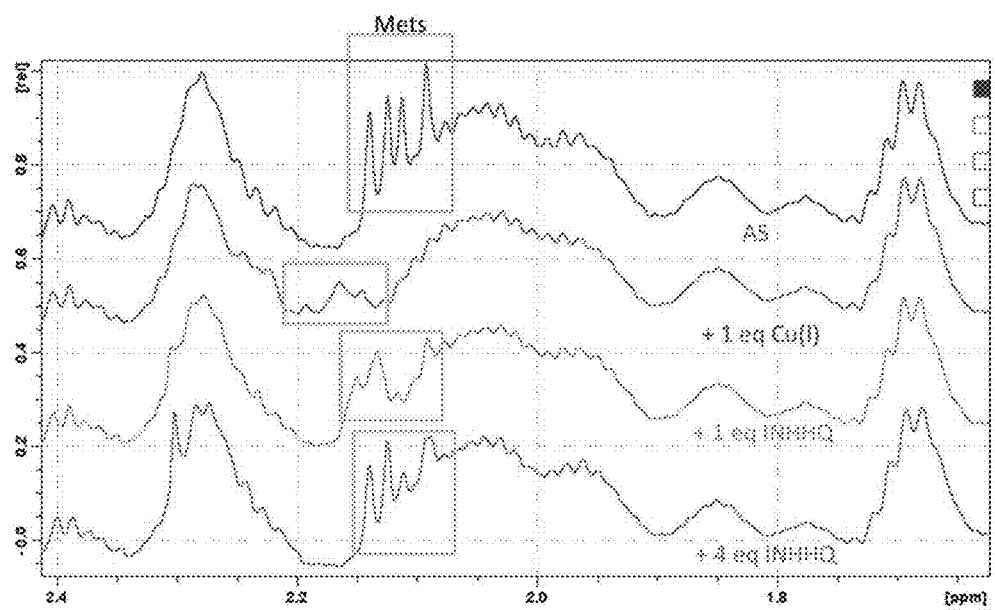
FIG. 7: $^1H$ NMR spectra showing that the addition of INHHQ (4 eq.) to a mixture containing α-synuclein and Cu(II)/Cu(I) (1 eq.) leads to the recovery of the original methionine signals' position; it is worth noting that methionine residues are the interaction point of copper with α-synuclein, which constitutes an indicative that INHHQ weakens Cu(II) or Cu(I)-α-synuclein interactions.

The experimental FTIR and Raman spectra of INHHQ, in the solid state, are shown in FIG. 5. The observed and calculated frequencies, as well as an attempt to assign the main bands, are given in Table 4.

TABLE 4

Assignment of the FTIR and Raman spectra of INHHQ (scale factor: 0.9381)

| Experimental (cm$^{-1}$) | | Theoretical (cm$^{-1}$) B3LYP/6-311 + G(d, p) | | | |
|---|---|---|---|---|---|
| FTIR | Raman | Unscaled (cm$^{-1}$) | Scaled (cm$^{-1}$) | IR Intensity | Vibrational Assignment |
| 3396 m | 3400 br | 3662 | 3435 | 104.3584 | ν OH |
| 3208 sh | 3205 w | | | — | |
| 3183 w | — | 3502 | 3285 | 5.5099 | ν NH |

TABLE 4-continued

Assignment of the FTIR and Raman spectra of INHHQ (scale factor: 0.9381)

| Experimental (cm⁻¹) FTIR | Raman | Theoretical (cm⁻¹) B3LYP/6-311 + G(d, p) Unscaled (cm⁻¹) | Scaled (cm⁻¹) | IR Intensity | Vibrational Assignment |
|---|---|---|---|---|---|
| 3148 sh | — | 3211/3205 | 3012/3007 | 1.8906/3.2991 | ν CH(Quin + Py)ip |
| 3073 sh | 3081 w | 3198 | 3000 | 9.2441 | ν CH(Quin)ip |
| 3059 sh | 3055 w | 3185/3178 | 2988/2981 | 18.7464/9.9528 | ν CH(Quin + Py)op |
| 3042 w | — | | | | — |
| 3028 sh | 3030 w | | | | — |
| 3016 w | — | | | | — |
| — | 2996 w | | | | — |
| 2959 sh | — | | | | — |
| 2923 w | — | | | | — |
| 2852 w | — | 3048 | 2859 | 40.4835 | νCH(Azomethine) |
| 2835 sh | — | | | | — |
| 1656 s | 1660 sh | 1767 | 1658 | 350.6350 | νC=O + βNH |
| 1647 vs | 1646 w | 1673 | 1569 | 20.7477 | ν C=N(Azomethine) + ν C=C(Quin) + βC—OH |
| 1604 w | 1603 vs | 1659 | 1556 | 2.3397 | ν C=N(Azomethine) + ν C=C(Quin) + βC—OH |
| 1595 w | 1595 s | 1634 | 1533 | 5.5690 | ν C=C(Quin) |
| 1556 m | 1555 w | 1597 | 1498 | 18.4149 | ν C=N(Quin) + νC=C(Quin) |
| 1545 m | — | 1630 | 1529 | 14.2312 | ν C=C(Py) + νC=N(Py) |
| 1507 m | 1507 w | 1555 | 1459 | 371.3416 | βNH + βCH(Quin) |
| 1490 w | 1488 vw | | | | — |
| 1465 m | 1468 w | 1541 | 1446 | 168.8474 | Ring stretch(Quin) + βC—OH + β NH |
| 1437 m | 1435 s | 1519 | 1425 | 6.8860 | βCH(Py) |
| 1407 w | — | | | | — |
| 1394 sh | 1396 m | | | | — |
| 1371 w | 1371 m | 1495 | 1402 | 176.2051 | β C—OH + β NH + β CH(Quin) |
| 1330 m | 1329 m | | | | — |
| 1299 s | 1304 m | 1360 | 1276 | 34.4059 | β CH(Quin + Azomethine) + ν C=N(Quin) + ν C—OH |
| 1280 m | 1279 sh | 1347 | 1264 | 31.7632 | β NH + β CH(Azomethine + Py) + β C—OH |
| 1270 sh | — | | | | — |
| 1252 m | 1252 s | 1309 | 1228 | 15.0576 | β CH(Quin + Azomethyne) + β C—OH |
| 1232 m | — | 1284 | 1205 | 117.6910 | ν C—OH + β CH(Quin + Azomethine) |
| 1217 w | 1220 w | 1278 | 1199 | 32.0853 | ν C=N(Py) + νC=C(Py) + β NH |
| 1204 w | 1204 vw | 1267 | 1189 | 56.8637 | β CH(Azomethine + Quin) + β C—OH |
| 1170 w | 1172 sh | 1253 | 1175 | 303.5474 | βCH(Py) + βNH |
| 1156 m | 1156 m | 1172 | 1099 | 380.9402 | ν N—N + βCH(Py + Quin) |
| 1136 w | 1133 w | 1112 | 1043 | 10.8679 | βCH(Py) |
| 1122 sh | — | | | | — |
| 1105 w | 1105 vw | | | | — |
| 1090 w | 1093 vw | 1109 | 1040 | 19.7634 | βCH(Py + Quin) |
| 1072 w | 1076 w | 1092 | 1024 | 9.3109 | βCH(Py) |
| — | 1063 vw | 1079 | 1012 | 11.9293 | βCH(Quin) + δ NNC |
| 1044 vw | 1044 vw | 1068 | 1002 | 1.6514 | βCH(Quin) |
| 1007 vw | — | | | | — |
| 992 vw | 992 w | 1010 | 947 | 1.7715 | Ring breath(Py) |
| 981 vw | — | 1008 | 946 | 1.5921 | γCH(Py) |
| 950 vw | 952 w | 959 | 900 | 14.8080 | γCH(Azomethine) |
| 931 w | 932 w | 914 | 857 | 2.9777 | Ring-deformation(Quin + Py) |
| 895 w | 897 vw | | | | — |
| 881 vw | — | | | | — |
| 867 w | 869 w | 898 | 842 | 0.0665 | γCH(Quin) |
| 856 m | 855 sh | 880 | 826 | 11.8041 | Ring-deformation(Quin + Py) |
| 837 m | 835 vw | 892 | 837 | 2.8606 | γCH(Py) |
| — | 812 vw | 804 | 754 | 2.0048 | γ C=C—C(Quin) + γ C=N—C(Quin) |
| 792 vw | 780 w | 789 | 740 | 5.7350 | β C=C—C(Quin + Azomethine) |
| 766 s | 768 vw | 767 | 720 | 9.2858 | γCH(Py) |
| 720 m | 720 m | 734 | 689 | 18.7702 | Ring-deformation(Quin) |
| 696 w | 696 vw | 763 | 716 | 38.2602 | γ CH(Quin) |

TABLE 4-continued

Assignment of the FTIR and Raman spectra of INHHQ (scale factor: 0.9381)

| Experimental (cm$^{-1}$) FTIR | Raman | Theoretical (cm$^{-1}$) B3LYP/6-311 + G(d, p) Unscaled (cm$^{-1}$) | Scaled (cm$^{-1}$) | IR Intensity | Vibrational Assignment |
|---|---|---|---|---|---|
| 677 s | — | 719 | 674 | 19.3631 | β C=N—C(Py) + β C=C—C(Quin) |
| 670 sh | 668 w | 698 | 655 | 2.0785 | γ C=C—C(Quin) + β C=N—C(Py) |
| 656 w | 657 w | 693 | 650 | 58.0279 | Ring-deformation(Py) |
| 644 sh | — | 681 | 639 | 1.5003 | Ring-deformation(Py) |
| 616 vw | — | 627 | 588 | 2.3638 | Ring-deformation(Quin) |
| 587 m | — | 604 | 567 | 90.9456 | γ OH |
| 575 w | — | | | | |
| 547 sh | 553 w | 588 | 552 | 10.5255 | β C=C—C(Quin) |
| 532 sh | 533 vw | 559 | 524 | 1.6705 | β C=C—C(Quin) + γ NH |
| 522 w | 523 vw | 551 | 517 | 14.1393 | γCH(Quin) + β C=C—C(Quin) + β C—OH |
| 482 w | 485 w | 539/534 | 506/501 | 16.0281/30.1104 | γ NH + γ C=C—C(Quin) |

Quin: quinoline ring; Py: pyridine ring; vs: very strong; s: strong; m: medium; w: weak; vw: very weak; br: broad; sh: shoulder; ip: in-phase; op: out-of-phase; v: stretching; β: in-plane bending; γ: out-of-plane bending.

Carbonylic C=O Stretching

The v C=O absorption is usually one of the most representative in an infrared spectrum and is also likely its most intense spectral feature. It appears in a wavenumber region relatively free of other vibrations (1800-1600 cm$^{-1}$). On the other hand, this mode gives only weak or very weak absorptions in Raman spectroscopy. In our study, as expected, v C=O vibration originates one of the strongest bands of the infrared spectrum, at 1656 cm$^{-1}$, which is in excellent agreement with the calculated value of 1658 cm$^{-1}$ (DFT calculations show a coupling between v C=O and β NH vibrations).

This mode was assigned at 1663 cm$^{-1}$ by Liu and Yang.

Azomethine C=N Stretching

The C=N stretchings of azomethine groups show absorptions close to that of carbonyl stretching. This fact can difficult an accurate assignment. For example, the C=N stretching bands of alkylated Schiff bases are usually found in the range 1674-1649 cm$^{-1}$, inside the common region of v C=O absorption. If conjugations of the C=N moiety with phenyl groups are present, the stretching frequency shifts to 1650-1600 cm$^{-1}$. In this work, two frequencies involving azomethine C=N vibrations were calculated (1569/1556 cm$^{-1}$), both of them coupled to v C=C of the quinoline ring and, to a lesser extent, to the phenol v C—OH. These values are in good agreement with the experimental frequencies observed in the infrared, at 1647 (vs) and 1604 (w) cm$^{-1}$, and Raman spectra, at 1646 (w) and 1603 (vs) cm$^{-1}$, respectively.

Liu and Yang, though, attributed this mode to a single band at 1613 cm$^{-1}$ in the IR spectrum, which was not observed in our study.

OH and NH Stretching Vibrations

OH and NH groups are very characteristic and their stretching vibrations are observed, in many cases, around 3500-3300 cm$^{-1}$. This absorption, however, is highly influenced by chemical environment, mainly when OH or NH groups are involved in hydrogen bonding. This can occur within the same molecule (intramolecular H bonding) or with adjacent molecules (intermolecular H bonding). The presence of intramolecular H bonding causes a thinning of the band and makes its position unaffected by concentration changes. In the IR spectrum of INHHQ, we observed a sharp band of medium intensity located at 3396 cm$^{-1}$, assigned to v OH. A similar absorption, at 3418 cm$^{-1}$, was reported by Krishnakumar and Ramasamy in the infrared spectrum of 8-hydroxyquinoline (8-HQ). On the other hand, intermolecular hydrogen bonding usually leads to a broadening of the band, as can be seen in the case of the v NH absorption of INHHQ, which was attributed to the weak IR band at 3183 cm$^{-1}$. In a previous study on the isonicotinoyl hydrazone of 2-hydroxy-3-methoxybenzaldehyde, published by us, v NH vibration was observed as a weak band at 3157 cm$^{-1}$. Here, we found serious discrepancies concerning the assignments made by Liu and Yang, since these authors attributed an absorption of higher frequency (reported by them at 3576 cm$^{-1}$) to the NH stretching mode, whereas the lower frequency band at 3193 cm$^{-1}$ was credited to the OH stretching movement.

Phenol C—OH Vibrations

In this work, the C—OH stretching mode was assigned to the medium intensity infrared band at 1232 cm$^{-1}$. This vibration is Raman inactive and had its frequency calculated at 1205 cm$^{-1}$. A coupled mode involving this movement was also predicted at 1276 cm$^{-1}$ [experimental: 1299 (infrared) cm$^{-1}$ and 1304 (Raman) cm$^{-1}$]. Another important vibration concerning the phenol group is the in-plane bending, which typically appears in the region 1440-1260 cm$^{-1}$, attributed to the weak infrared band (medium in the Raman spectrum) at 1371 cm$^{-1}$. Coupled modes are observed in FTIR at 1465, 1280, 1252 and 1202 cm$^{-1}$. Theoretical and experimental frequencies show good agreement (Table 4).

Biological Activity Studies

This hydrazonic compound has the ability, as proved by 1D and 2D NMR experiments, of compete with the β-amyloid peptide (or α-synuclein), key-targets, respectively, in Alzheimer's and Parkinson's diseases, by physiological ions such as $Zn^{2+}$ $Cu^{2+}$ and $Cu^+$, which can cause their precipitation or oligomerization and contribute to worsen the oxidative stress condition observed in the brains of patients suffering from these neurodegenerative disorders. INHHQ does not interact directly with the β-amyloid peptide and α-synuclein, nonetheless inhibits the interactions between these targets and metals through a mechanism that probably involves metal ion sequestering.

In silico pharmacological analyses (mandatory studies in the development of new therapeutic agents, whose aim is to predict pharmacokinetic properties of novel molecules with a potential pharmacological action) show that the Lipinski's parameters presented by INHHQ (Table 5), calculated via 1D-QSAR method, are in agreement to ideal values, suggesting that this compound constitutes an excellent candidate to new drug, with good oral absorption and cellular permeability. The model also indicates that INHHQ possesses structural features which can allow it crossing the blood-brain barrier (BBB), resulting in therapeutic actions inside the patients' brains.

TABLE 5

Lipinski parameters calculated for INHHQ, along with reference values

| Parameters | INHHQ | Ref. Oral Biodisponibility | Ref. BBB Crossing |
|---|---|---|---|
| HBD | 2 | ≤5 | ≤3 |
| HBA | 6 | ≤10 | ≤7 |
| MW | 292 | ≤500 | ≤400 |
| log P | 2.34 | −1 a 5 | −1 a 5 |
| log D (pH = 7.4) | 2.27 | −1 a 5 | −1 a 5 |
| log S | −3.36 | −4 a 2 | −4 a 2 |
| PSA | 66.077 Å | ≤140 Å | ≤90 Å |
| Rotatable bonds | 4 | ≤10 | ≤10 |

Furthermore, both the INHHQ molecule itself and its potential metabolites were shown, in theoretical comparison with the toxic fragments of over 3000 commercially available drugs, completely non-toxic.

In fact, the intraperitoneal injection of up to 300 mg kg$^{-1}$ of the compound, using 10% DMSO/saline solution as vehicle of injection, in Wistar male rats (acute toxicity test) showed that INHHQ was apparently not toxic to the animals throughout the 72 h of the experiment: no animals died and there were no behavioral changes noted in the injected rats. Also, after the animals' sacrifice, there were no macroscopic abnormalities observed during its organs dissection.

The invention claimed is:
1. A crystalline polymorph of the anhydrous form, comprising:
I—the crystal structure of FIG. 1:
II—crystal packing comprising one or more of the following features:
(a) maintained by intermolecular H bonds involving the carbonyl oxygen O2 (acceptor) of a molecule and the N2-H group of the following molecule [moderate N2 . . . O2$^i$=2,966 Å, symmetry codes: (i) −x+½, y−½, z], connecting the molecules of INHHQ in zigzag chains; or
(b) molecules in each chain interconnected by cross-stacking π-π interactions involving the quinoline rings, being the calculated centroid-centroid distance equal to 3.8303(9) Å, and the adjacent chains interconnected by O1-H12 . . . π interactions; or
(c) as a result of the mentioned O1-H12 . . . π interactions, zigzag columns run parallel to the crystallographic axis a; and
III—the following characteristics:

| Melting point | 246-249° C. |
|---|---|
| Elemental analysis | C, 66.3%; H, 4.1%; N, 19.4% |
| Crystal system | Orthorhombic |

-continued

| Unit cell size | a = 17.0761(4) Å |
|---|---|
| | b = 8.25480(10) Å |
| | c = 19.3549(4) Å |
| Z | 8 |
| ρ (calculated) | 1.423 g cm$^{-3}$. |

2. The crystalline polymorph of the anhydrous form according to claim 1, presenting X-ray diffraction peaks (2θ ranging from 10.5 to 70.5°) as follows:

| Plane (h, k, l) | | | Multiplicity | Interplanar distance (Å) | 2 theta (°) |
|---|---|---|---|---|---|
| H | k | l | m | d | |
| 1 | 0 | 0 | 2 | 8.34877 | 10.58783 |
| 0 | 1 | 0 | 2 | 7.07920 | 12.49361 |
| 0 | 1 | 1 | 4 | 5.94931 | 14.87873 |
| 1 | 0 | −2 | 2 | 5.93863 | 14.90564 |
| 1 | −1 | −1 | 4 | 5.50433 | 16.08920 |
| 0 | 0 | 2 | 2 | 5.48852 | 16.13588 |
| 1 | 1 | 0 | 4 | 5.39942 | 16.40394 |
| 1 | −1 | −2 | 4 | 4.54974 | 19.49495 |
| 1 | 1 | 1 | 4 | 4.37713 | 20.27167 |
| 2 | 0 | −2 | 2 | 4.37659 | 20.27421 |
| 0 | 1 | 2 | 4 | 4.33757 | 20.45853 |
| 2 | 0 | 0 | 2 | 4.17439 | 21.26742 |
| 2 | −1 | −1 | 4 | 3.87923 | 22.90666 |
| 1 | 0 | 2 | 2 | 3.87110 | 22.95541 |
| 2 | −1 | −2 | 4 | 3.72262 | 23.88427 |
| 2 | 1 | 0 | 4 | 3.59579 | 24.73979 |
| 0 | 2 | 0 | 2 | 3.53960 | 25.13890 |
| 1 | −1 | −3 | 4 | 3.53090 | 25.20189 |
| 1 | 1 | 2 | 4 | 3.39646 | 26.21681 |
| 0 | 2 | 1 | 4 | 3.36879 | 26.43604 |
| 1 | −2 | −1 | 4 | 3.28146 | 27.15290 |
| 1 | 2 | 0 | 4 | 3.25881 | 27.34522 |
| 2 | −1 | −3 | 4 | 3.25355 | 27.39035 |
| 0 | 1 | 3 | 4 | 3.25049 | 27.41659 |
| 3 | 0 | −2 | 2 | 3.08971 | 28.87348 |
| 2 | 1 | 1 | 4 | 3.08859 | 28.88417 |
| 1 | −2 | −2 | 4 | 3.04049 | 29.35123 |
| 1 | 0 | −4 | 2 | 3.03231 | 29.43221 |
| 1 | 2 | 1 | 4 | 2.98732 | 29.88574 |
| 0 | 2 | 2 | 4 | 2.97465 | 30.01599 |
| 2 | 0 | −4 | 2 | 2.96931 | 30.07124 |
| 3 | −1 | −2 | 4 | 2.83175 | 31.56923 |
| 2 | −2 | −1 | 4 | 2.81367 | 31.77739 |
| 3 | −1 | −1 | 4 | 2.78865 | 32.07025 |
| 1 | −1 | −4 | 4 | 2.78737 | 32.08534 |
| 2 | 0 | 2 | 2 | 2.78466 | 32.11737 |
| 3 | 0 | 0 | 2 | 2.78292 | 32.13796 |
| 2 | −2 | −2 | 4 | 2.75217 | 32.50702 |
| 0 | 0 | 4 | 2 | 2.74426 | 32.60332 |
| 2 | −1 | −4 | 4 | 2.73820 | 32.67747 |
| 2 | 2 | 0 | 4 | 2.69971 | 33.15667 |
| 3 | −1 | −3 | 4 | 2.69759 | 33.18355 |
| 1 | 1 | 3 | 4 | 2.69411 | 33.22766 |
| 1 | −2 | −3 | 4 | 2.67192 | 33.51166 |
| 1 | 2 | 2 | 4 | 2.61222 | 34.30092 |
| 3 | 0 | −4 | 2 | 2.61018 | 34.32857 |
| 2 | 1 | 2 | 4 | 2.59139 | 34.58541 |
| 3 | 1 | 0 | 4 | 2.58999 | 34.60470 |
| 0 | 1 | 4 | 4 | 2.55873 | 35.04100 |
| 2 | −2 | −3 | 4 | 2.54551 | 35.22898 |
| 0 | 2 | 3 | 4 | 2.54404 | 35.24991 |
| 2 | 2 | 1 | 4 | 2.46414 | 36.43237 |
| 3 | −1 | −4 | 4 | 2.44902 | 36.66531 |
| 0 | 3 | 0 | 2 | 2.35973 | 38.10499 |
| 3 | −2 | −2 | 4 | 2.32767 | 38.65065 |
| 1 | 0 | 4 | 2 | 2.32176 | 38.75283 |
| 4 | 0 | −2 | 2 | 2.31874 | 38.80530 |
| 3 | 1 | 1 | 4 | 2.31772 | 38.82317 |
| 0 | 3 | 1 | 4 | 2.30703 | 39.01032 |
| 3 | −2 | −1 | 4 | 2.30355 | 39.07167 |
| 1 | −2 | −4 | 4 | 2.30283 | 39.08438 |
| 2 | −1 | −5 | 4 | 2.30097 | 39.11728 |

-continued

| Plane (h, k, l) | | | Multiplicity | Interplanar distance (Å) | 2 theta (°) |
|---|---|---|---|---|---|
| H | k | l | m | d | |
| 1 | −3 | −1 | 4 | 2.27839 | 39.52090 |
| 2 | −2 | −4 | 4 | 2.27487 | 39.58469 |
| 1 | −1 | −5 | 4 | 2.27151 | 39.64563 |
| 1 | 3 | 0 | 4 | 2.27077 | 39.65907 |
| 3 | −2 | −3 | 4 | 2.25142 | 40.01449 |
| 1 | 2 | 3 | 4 | 2.24939 | 40.05204 |
| 1 | 1 | 4 | 4 | 2.20614 | 40.87197 |
| 4 | −1 | −2 | 4 | 2.20355 | 40.92216 |
| 1 | −3 | −2 | 4 | 2.19295 | 41.12888 |
| 2 | 2 | 2 | 4 | 2.18856 | 41.21509 |
| 4 | 0 | −4 | 2 | 2.18829 | 41.22042 |
| 3 | 2 | 0 | 4 | 2.18772 | 41.23171 |
| 4 | −1 | −3 | 4 | 2.18705 | 41.24487 |
| 2 | 1 | 3 | 4 | 2.18427 | 41.29979 |
| 1 | 3 | 1 | 4 | 2.17275 | 41.52890 |
| 0 | 2 | 4 | 4 | 2.16879 | 41.60831 |
| 3 | −1 | −5 | 4 | 2.16859 | 41.61228 |
| 0 | 3 | 2 | 4 | 2.16786 | 41.62688 |
| 4 | −1 | −1 | 4 | 2.13480 | 42.30230 |
| 3 | 0 | 2 | 2 | 2.13258 | 42.34844 |
| 2 | −3 | −1 | 4 | 2.10312 | 42.97079 |
| 3 | −2 | −4 | 4 | 2.10076 | 43.02150 |
| 0 | 1 | 5 | 4 | 2.09689 | 43.10495 |
| 4 | −1 | −4 | 4 | 2.09069 | 43.23919 |
| 4 | 0 | 0 | 2 | 2.08719 | 43.31522 |
| 2 | −3 | −2 | 4 | 2.07706 | 43.53728 |
| 2 | 3 | 0 | 4 | 2.05423 | 44.04625 |
| 3 | 1 | 2 | 4 | 2.04194 | 44.32549 |
| 1 | −3 | −3 | 4 | 2.04191 | 44.32613 |
| 2 | 0 | −6 | 2 | 2.03690 | 44.44102 |
| 3 | 2 | 1 | 4 | 2.01612 | 44.92393 |
| 1 | 3 | 2 | 4 | 2.01489 | 44.95273 |
| 2 | −2 | −5 | 4 | 2.00506 | 45.18528 |
| 4 | 1 | 0 | 4 | 2.00199 | 45.25840 |
| 1 | −2 | −5 | 4 | 1.98548 | 45.65592 |
| 2 | −3 | −3 | 4 | 1.98380 | 45.69690 |
| 0 | 3 | 3 | 4 | 1.98310 | 45.71378 |
| 3 | 0 | −6 | 2 | 1.97954 | 45.80066 |
| 1 | 0 | −6 | 2 | 1.97817 | 45.83434 |
| 2 | −1 | −6 | 4 | 1.95748 | 46.34679 |
| 2 | 3 | 1 | 4 | 1.94455 | 46.67316 |
| 4 | −1 | −5 | 4 | 1.94222 | 46.73259 |
| 1 | 2 | 4 | 4 | 1.94138 | 46.75385 |
| 4 | −2 | −2 | 4 | 1.93962 | 46.79894 |
| 2 | 0 | 4 | 2 | 1.93555 | 46.90307 |
| 4 | −2 | −3 | 4 | 1.92834 | 47.08917 |
| 2 | 2 | 3 | 4 | 1.92643 | 47.13862 |
| 3 | −2 | −5 | 4 | 1.91564 | 47.42022 |
| 3 | −1 | −6 | 4 | 1.90641 | 47.66401 |
| 1 | −1 | −6 | 4 | 1.90518 | 47.69668 |
| 4 | −2 | −1 | 4 | 1.89223 | 48.04363 |
| 3 | −3 | −2 | 4 | 1.87535 | 48.50388 |
| 2 | 1 | 4 | 4 | 1.86703 | 48.73407 |
| 0 | 2 | 5 | 4 | 1.86568 | 48.77150 |
| 3 | −3 | −1 | 4 | 1.86266 | 48.85561 |
| 1 | −3 | −4 | 4 | 1.86228 | 48.86626 |
| 4 | −2 | −4 | 4 | 1.86131 | 48.89351 |
| 1 | 1 | 5 | 4 | 1.85776 | 48.99309 |
| 2 | −3 | −4 | 4 | 1.84740 | 49.28595 |
| 5 | 0 | −2 | 2 | 1.83827 | 49.54725 |
| 4 | 1 | 1 | 4 | 1.83748 | 49.56990 |
| 3 | −3 | −3 | 4 | 1.83478 | 49.64793 |
| 1 | 3 | 3 | 4 | 1.83368 | 49.67962 |
| 4 | 0 | −6 | 2 | 1.83168 | 49.73747 |
| 0 | 0 | 6 | 2 | 1.82951 | 49.80075 |
| 5 | 0 | −4 | 2 | 1.82704 | 49.87241 |
| 3 | 2 | 2 | 4 | 1.82666 | 49.88361 |
| 2 | 3 | 2 | 4 | 1.80028 | 50.66584 |
| 3 | 3 | 0 | 4 | 1.79981 | 50.68000 |
| 4 | 2 | 0 | 4 | 1.79790 | 50.73774 |
| 5 | −1 | −3 | 4 | 1.79778 | 50.74113 |
| 3 | 1 | 3 | 4 | 1.79572 | 50.80350 |
| 0 | 3 | 4 | 4 | 1.78922 | 51.00132 |
| 5 | −1 | −2 | 4 | 1.77926 | 51.30747 |
| 4 | −1 | −6 | 4 | 1.77329 | 51.49295 |
| 0 | 1 | 6 | 4 | 1.77131 | 51.55465 |
| 0 | 4 | 0 | 2 | 1.76980 | 51.60187 |
| 5 | −1 | −4 | 4 | 1.76908 | 51.62454 |
| 2 | −2 | −6 | 4 | 1.76545 | 51.73845 |
| 4 | −2 | −5 | 4 | 1.75423 | 52.09423 |
| 3 | −3 | −4 | 4 | 1.75045 | 52.21513 |
| 0 | 4 | 1 | 4 | 1.74724 | 52.31836 |
| 1 | −4 | −1 | 4 | 1.73470 | 52.72556 |
| 1 | 4 | 0 | 4 | 1.73133 | 52.83614 |
| 3 | −2 | −6 | 4 | 1.72771 | 52.95534 |
| 1 | −2 | −6 | 4 | 1.72680 | 52.98560 |
| 5 | −1 | −1 | 4 | 1.71763 | 53.29042 |
| 4 | 0 | 2 | 2 | 1.71625 | 53.33669 |
| 3 | 3 | 1 | 4 | 1.70057 | 53.86813 |
| 5 | −1 | −5 | 4 | 1.69944 | 53.90672 |
| 2 | 2 | 4 | 4 | 1.69823 | 53.94829 |
| 1 | −4 | −2 | 4 | 1.69608 | 54.02211 |
| 2 | −3 | −5 | 4 | 1.69392 | 54.09682 |
| 1 | 2 | 5 | 4 | 1.69125 | 54.18921 |
| 2 | −1 | −7 | 4 | 1.69108 | 54.19489 |
| 1 | 4 | 1 | 4 | 1.68669 | 54.34788 |
| 0 | 4 | 2 | 4 | 1.68440 | 54.42786 |
| 1 | −3 | −5 | 4 | 1.68206 | 54.50961 |
| 3 | −1 | −7 | 4 | 1.68013 | 54.57753 |
| 4 | 2 | 1 | 4 | 1.67591 | 54.72649 |
| 5 | 0 | 0 | 2 | 1.66975 | 54.94516 |
| 4 | 1 | 2 | 4 | 1.66794 | 55.01012 |
| 1 | 3 | 4 | 4 | 1.65500 | 55.47716 |
| 4 | −3 | −2 | 4 | 1.65390 | 55.51703 |
| 2 | −4 | −1 | 4 | 1.65348 | 55.53225 |
| 4 | −3 | −3 | 4 | 1.64689 | 55.77391 |
| 2 | 3 | 3 | 4 | 1.64570 | 55.81771 |
| 5 | −2 | −3 | 4 | 1.64562 | 55.82063 |
| 5 | 0 | −6 | 2 | 1.64485 | 55.84915 |
| 3 | 2 | 3 | 4 | 1.64404 | 55.87900 |
| 1 | 0 | 6 | 2 | 1.64248 | 55.93667 |
| 2 | −4 | −2 | 4 | 1.64073 | 56.00177 |
| 3 | −3 | −5 | 4 | 1.63896 | 56.06742 |
| 1 | −1 | −7 | 4 | 1.63562 | 56.19224 |
| 5 | −2 | −2 | 4 | 1.63138 | 56.35117 |
| 2 | 4 | 0 | 4 | 1.62941 | 56.42557 |
| 3 | 0 | 4 | 2 | 1.62858 | 56.45687 |
| 4 | −2 | −6 | 4 | 1.62677 | 56.52512 |
| 0 | 2 | 6 | 4 | 1.62525 | 56.58301 |
| 5 | 1 | 0 | 4 | 1.62516 | 56.58630 |
| 4 | −3 | −1 | 4 | 1.62423 | 56.62165 |
| 5 | −2 | −4 | 4 | 1.62352 | 56.64860 |
| 1 | −4 | −3 | 4 | 1.62324 | 56.65939 |
| 2 | 1 | 5 | 4 | 1.62060 | 56.76011 |
| 1 | 4 | 2 | 4 | 1.60956 | 57.18482 |
| 0 | 3 | 5 | 4 | 1.60734 | 57.27112 |
| 4 | −1 | −7 | 4 | 1.60639 | 57.30817 |
| 4 | −3 | −4 | 4 | 1.60455 | 57.38024 |
| 5 | −1 | −6 | 4 | 1.60217 | 57.47322 |
| 1 | 1 | 6 | 4 | 1.59998 | 57.55912 |
| 2 | −4 | −3 | 4 | 1.59358 | 57.81228 |
| 0 | 4 | 3 | 4 | 1.59322 | 57.82655 |
| 3 | 1 | 4 | 4 | 1.58712 | 58.06987 |
| 5 | −2 | −1 | 4 | 1.58349 | 58.21592 |
| 3 | 3 | 2 | 4 | 1.58219 | 58.26825 |
| 2 | 4 | 1 | 4 | 1.57302 | 58.64091 |
| 5 | −2 | −5 | 4 | 1.56920 | 58.79766 |
| 4 | 3 | 0 | 4 | 1.56339 | 59.03785 |
| 2 | −2 | −7 | 4 | 1.56261 | 59.07000 |
| 3 | −2 | −7 | 4 | 1.55396 | 59.43196 |
| 6 | 0 | −4 | 2 | 1.54485 | 59.81773 |
| 4 | 2 | 2 | 4 | 1.54429 | 59.84161 |
| 2 | −3 | −6 | 4 | 1.54191 | 59.94356 |
| 3 | −4 | −2 | 4 | 1.53571 | 60.21080 |
| 4 | −3 | −5 | 4 | 1.53442 | 60.26657 |
| 0 | 1 | 7 | 4 | 1.53103 | 60.41363 |
| 3 | −4 | −1 | 4 | 1.52872 | 60.51473 |
| 1 | −4 | −4 | 4 | 1.52851 | 60.52394 |

-continued

| Plane (h, k, l) | | | Multiplicity | Interplanar distance (Å) | 2 theta (°) |
|---|---|---|---|---|---|
| H | k | l | m | d | |
| 3 | 0 | −8 | 2 | 1.52498 | 60.67867 |
| 2 | −4 | −4 | 4 | 1.52025 | 60.88755 |
| 1 | −2 | −7 | 4 | 1.51854 | 60.96338 |
| 6 | 0 | −2 | 2 | 1.51698 | 61.03271 |
| 3 | −3 | −6 | 4 | 1.51658 | 61.05053 |
| 5 | 1 | 1 | 4 | 1.51638 | 61.05931 |
| 2 | 0 | −8 | 2 | 1.51616 | 61.06934 |
| 1 | −3 | −6 | 4 | 1.51596 | 61.07813 |
| 3 | −4 | −3 | 4 | 1.51319 | 61.20197 |
| 1 | 4 | 3 | 4 | 1.51257 | 61.22953 |
| 6 | −1 | −3 | 4 | 1.51024 | 61.33418 |
| 5 | 2 | 0 | 4 | 1.51016 | 61.33806 |
| 6 | −1 | −4 | 4 | 1.50933 | 61.37515 |
| 4 | 1 | 3 | 4 | 1.50872 | 61.40297 |
| 2 | 2 | 5 | 4 | 1.50649 | 61.50344 |
| 2 | 3 | 4 | 4 | 1.49652 | 61.95818 |
| 4 | −2 | −7 | 4 | 1.49506 | 62.02536 |
| 2 | 4 | 2 | 4 | 1.49366 | 62.09007 |
| 3 | 4 | 0 | 4 | 1.49339 | 62.10246 |
| 1 | 3 | 5 | 4 | 1.49174 | 62.17898 |
| 5 | −2 | −6 | 4 | 1.49166 | 62.18267 |
| 5 | −1 | −7 | 4 | 1.49157 | 62.18692 |
| 3 | −1 | −8 | 4 | 1.49078 | 62.22328 |
| 1 | 2 | 6 | 4 | 1.48989 | 62.26457 |
| 0 | 4 | 4 | 4 | 1.48733 | 62.38401 |
| 4 | 0 | −8 | 2 | 1.48466 | 62.50882 |
| 6 | −1 | −2 | 4 | 1.48331 | 62.57221 |
| 2 | −1 | −8 | 4 | 1.48254 | 62.60831 |
| 4 | 3 | 1 | 4 | 1.48118 | 62.67218 |
| 6 | −1 | −5 | 4 | 1.48072 | 62.69367 |
| 3 | 2 | 4 | 4 | 1.47949 | 62.75186 |
| 3 | −4 | −4 | 4 | 1.46483 | 63.45251 |
| 1 | 0 | −8 | 2 | 1.46062 | 63.65703 |
| 5 | −3 | −3 | 4 | 1.46015 | 63.67986 |
| 3 | 3 | 3 | 4 | 1.45904 | 63.73375 |
| 6 | 0 | −6 | 2 | 1.45886 | 63.74255 |
| 2 | 0 | 6 | 2 | 1.45666 | 63.85023 |
| 4 | −1 | −8 | 4 | 1.45305 | 64.02798 |
| 5 | −3 | −2 | 4 | 1.45017 | 64.17003 |
| 4 | −3 | −6 | 4 | 1.44693 | 64.33096 |
| 0 | 3 | 6 | 4 | 1.44586 | 64.38455 |
| 5 | −3 | −4 | 4 | 1.44464 | 64.44527 |
| 3 | 4 | 1 | 4 | 1.43522 | 64.91979 |
| 0 | 2 | 7 | 4 | 1.43374 | 64.99512 |
| 6 | −1 | −1 | 4 | 1.43271 | 65.04772 |
| 5 | 0 | 2 | 2 | 1.43178 | 65.09530 |
| 2 | −4 | −5 | 4 | 1.43122 | 65.12385 |
| 1 | −1 | −8 | 4 | 1.43049 | 65.16140 |
| 6 | −1 | −6 | 4 | 1.42884 | 65.24586 |
| 2 | 1 | 6 | 4 | 1.42677 | 65.35220 |
| 1 | −4 | −5 | 4 | 1.42405 | 65.49281 |
| 5 | 2 | 1 | 4 | 1.42169 | 65.61510 |
| 6 | −2 | −3 | 4 | 1.41663 | 65.87928 |
| 5 | −3 | −1 | 4 | 1.41622 | 65.90063 |
| 6 | −2 | −4 | 4 | 1.41588 | 65.91867 |
| 0 | 5 | 0 | 2 | 1.41584 | 65.92052 |
| 4 | 2 | 3 | 4 | 1.41537 | 65.94542 |
| 3 | 1 | 5 | 4 | 1.41356 | 66.04055 |
| 1 | 4 | 4 | 4 | 1.40751 | 66.36081 |
| 4 | −4 | −2 | 4 | 1.40684 | 66.39668 |
| 5 | −3 | −5 | 4 | 1.40597 | 66.44291 |
| 5 | 0 | −8 | 2 | 1.40574 | 66.45520 |
| 0 | 5 | 1 | 4 | 1.40421 | 66.53712 |
| 5 | 1 | 2 | 4 | 1.40336 | 66.58237 |
| 1 | 1 | 7 | 4 | 1.40288 | 66.60856 |
| 4 | −4 | −3 | 4 | 1.40251 | 66.62790 |
| 2 | 4 | 3 | 4 | 1.40178 | 66.66737 |
| 2 | −3 | −7 | 4 | 1.40123 | 66.69715 |
| 5 | −2 | −7 | 4 | 1.40118 | 66.69978 |
| 3 | −2 | −8 | 4 | 1.40053 | 66.73479 |
| 1 | −5 | −1 | 4 | 1.39767 | 66.88894 |
| 3 | −4 | −5 | 4 | 1.39761 | 66.89248 |
| 1 | 5 | 0 | 4 | 1.39591 | 66.98464 |
| 3 | −3 | −7 | 4 | 1.39498 | 67.03543 |
| 6 | −2 | −2 | 4 | 1.39432 | 67.07096 |
| 2 | −2 | −8 | 4 | 1.39368 | 67.10576 |
| 4 | 0 | 4 | 2 | 1.39233 | 67.17963 |
| 6 | −2 | −5 | 4 | 1.39218 | 67.18803 |
| 6 | 0 | 0 | 2 | 1.39146 | 67.22715 |
| 4 | −4 | −1 | 4 | 1.38844 | 67.39312 |
| 4 | 3 | 2 | 4 | 1.38797 | 67.41877 |
| 5 | −1 | −8 | 4 | 1.37882 | 67.92709 |
| 0 | 4 | 5 | 4 | 1.37785 | 67.98154 |
| 1 | −5 | −2 | 4 | 1.37724 | 68.01559 |
| 4 | −4 | −4 | 4 | 1.37608 | 68.08057 |
| 1 | 5 | 1 | 4 | 1.37219 | 68.30019 |
| 0 | 0 | 8 | 2 | 1.37213 | 68.30382 |
| 0 | 5 | 2 | 4 | 1.37096 | 68.37016 |
| 1 | −3 | −7 | 4 | 1.36918 | 68.47118 |
| 4 | −2 | −8 | 4 | 1.36910 | 68.47589 |
| 4 | 1 | 4 | 4 | 1.36616 | 68.64389 |
| 6 | 1 | 0 | 4 | 1.36534 | 68.69093 |
| 5 | 3 | 0 | 4 | 1.36303 | 68.82355 |
| 3 | 4 | 2 | 4 | 1.36190 | 68.88850 |
| 6 | −1 | −7 | 4 | 1.36065 | 68.96085 |
| 2 | 3 | 5 | 4 | 1.36033 | 68.97921 |
| 2 | −5 | −1 | 4 | 1.35414 | 69.33989 |
| 6 | −2 | −1 | 4 | 1.35205 | 69.46230 |
| 4 | −3 | −7 | 4 | 1.35190 | 69.47100 |
| 1 | −2 | −8 | 4 | 1.35018 | 69.57237 |
| 4 | 4 | 0 | 4 | 1.34986 | 69.59140 |
| 5 | −3 | −6 | 4 | 1.34938 | 69.61938 |
| 6 | −2 | −6 | 4 | 1.34879 | 69.65417 |
| 1 | 3 | 6 | 4 | 1.34807 | 69.69667 |
| 2 | −5 | −2 | 4 | 1.34710 | 69.75419 |
| 0 | 1 | 8 | 4 | 1.34706 | 69.75684 |
| 2 | 2 | 6 | 4 | 1.34705 | 69.75717 |
| 2 | 5 | 0 | 4 | 1.34082 | 70.12915 |
| 3 | 3 | 4 | 4 | 1.34035 | 70.15689 |
| 1 | −5 | −3 | 4 | 1.33737 | 70.33644 |
| 2 | −4 | −6 | 4 | 1.33596 | 70.42175 |
| 3 | 2 | 5 | 4 | 1.33592 | 70.42439. |

3. The crystalline polymorph of the anhydrous form according to claim 1, further comprising the infrared spectrum FIG. 5.

4. The crystalline polymorph of the anhydrous form according to claim 1, presenting the next IR vibrational frequencies:
C═O stretching at 1656 cm$^{-1}$; and
azomethine C═N stretching at 1647 cm$^{-1}$ and 1604 cm$^{-1}$; and
OH stretching at 3396 cm$^{-1}$; and
NH stretching at 3183 cm$^{-1}$.

5. The crystalline polymorph of the anhydrous form according to claim 4, further comprising the infrared spectrum FIG. 5.

6. A pharmaceutical composition comprising the anhydrous crystalline polymorph as described in claim 1, 2, 3, 4, or 5, further comprising, at least one of a diluent, an excipient, and any pharmaceutically acceptable vehicle.

* * * * *